US008846387B2

(12) United States Patent
Russell et al.

(10) Patent No.: US 8,846,387 B2
(45) Date of Patent: Sep. 30, 2014

(54) TARGETED GENE MODIFICATION BY PARVOVIRAL VECTORS

(75) Inventors: David W. Russell, Seattle, WA (US); Roli K. Hirata, Seattle, WA (US)

(73) Assignee: The University of Washington, Seattle, WA (US)

( * ) Notice: Subject to any disclaimer, the term of this patent is extended or adjusted under 35 U.S.C. 154(b) by 0 days.

(21) Appl. No.: 13/114,117

(22) Filed: May 24, 2011

(65) Prior Publication Data

US 2012/0070890 A1 Mar. 22, 2012

Related U.S. Application Data

(63) Continuation of application No. 10/423,604, filed on Apr. 24, 2003, now Pat. No. 7,972,856, which is a continuation of application No. 09/428,172, filed on Oct. 27, 1999, now abandoned, which is a continuation-in-part of application No. PCT/US98/07964, filed on Apr. 20, 1998.

(60) Provisional application No. 60/106,191, filed on Oct. 28, 1998, provisional application No. 60/044,789, filed on Apr. 24, 1997.

(51) Int. Cl.
| | |
|---|---|
| *C12N 15/00* | (2006.01) |
| *C12N 15/63* | (2006.01) |
| *C12N 15/87* | (2006.01) |
| *A01N 63/00* | (2006.01) |
| *C12N 15/86* | (2006.01) |
| *A01K 67/00* | (2006.01) |

(52) U.S. Cl.
CPC ...... *C12N 15/86* (2013.01); *C12N 2750/14143* (2013.01)
USPC ........................ 435/320.1; 435/463; 424/93.2

(58) Field of Classification Search
USPC ................ 435/320.1, 463; 424/93.2
See application file for complete search history.

(56) References Cited

U.S. PATENT DOCUMENTS

| | | | |
|---|---|---|---|
| 5,340,740 A | | 8/1994 | Petitte et al. |
| 5,455,169 A | | 10/1995 | Mullan |
| 5,468,629 A | | 11/1995 | Calhoun |
| 5,585,254 A | | 12/1996 | Maxwell et al. |
| 5,602,307 A | | 2/1997 | Beaudet et al. |
| 5,604,090 A | | 2/1997 | Alexander et al. |
| 5,614,396 A | | 3/1997 | Bradley et al. |
| 5,631,153 A | | 5/1997 | Capecchi et al. |
| 5,658,776 A | * | 8/1997 | Flotte et al. .................. 435/457 |
| 5,763,240 A | | 6/1998 | Zarling et al. |
| 5,773,289 A | | 6/1998 | Samulski et al. |
| 5,801,030 A | | 9/1998 | McVey et al. |
| 5,814,300 A | * | 9/1998 | Scott et al. ..................... 800/3 |
| 6,147,276 A | | 11/2000 | Campbell et al. |
| 6,200,806 B1 | | 3/2001 | Thomson |
| 6,528,313 B1 | | 3/2003 | Le Mouellic et al. |
| 6,528,314 B1 | | 3/2003 | Le Mouellic et al. |
| 6,638,768 B1 | | 10/2003 | Le Mouellic et al. |
| 2001/0051611 A1 | | 12/2001 | Srivastava et al. |
| 2004/0203153 A1 | | 10/2004 | Le Mouellic et al. |
| 2004/0250301 A1 | | 12/2004 | Mouellic et al. |

FOREIGN PATENT DOCUMENTS

| | | |
|---|---|---|
| WO | 90/11354 A1 | 10/1990 |
| WO | WO 93/22426 | 11/1993 |
| WO | WO 94/26884 | 11/1994 |
| WO | WO 97/47756 | 12/1997 |
| WO | 98/48005 A1 | 10/1998 |
| WO | 00/24917 A1 | 5/2000 |
| WO | 02/091866 A1 | 11/2002 |

OTHER PUBLICATIONS

Difoot et al. Identical ends are not required for the equal encapsidation of Plus- and Minus-Strand parvovirus LuIII DNA. J. Virol. 63:3180-3184, 1989.*
Porter, Mol Therapy, 3:423-424 (2001). "Correcting a deficiency."
Verma et al., Gene Therapy, Annu Rev Biochem, 74:711-738 (2005). "Gene therapy: twenty-first century medicine."
Wang et al., J Virol, 70:1668-1677 (1996). "Rescue and replication of adeno-associated virus type 2 as well as vector DNA secuences from recombinant plasmids containing deletions in the viral inverted terminal repeats: selective encapsidation of viral genomes in progeny virions."
Dang et al., "Gene Therapy and Translational Cancer Research," Clin. Cancer Res. 5:471-474 (1999).
Deonarain, "Ligand-Targeted Receptor-Mediated Vectors for Gene Delivery," Exp. Opin. Ther. Pat. 8(1):53-69 (1998).
Dewhurst, "Parvoviruses: Basics," http://www.urmc.rochesteredu/smd/mbi/grad2/parvo97.html (Oct. 1996).
Gerson, "Mesenchymal Stem Cells: No Longer Second Class Marrow Citizens," Nat. Med. 5(3):262-264 (1999).
Kestler et al., "Cis Requirements for the Efficient Production of Recombinant DNA Vectors Based on Autonomous Parvoviruses," Human gene Ther. 10(10):1619-1632 (1999).
Leff, "Adeno-Associated Viral Vector Fixes Mutant Genes, Removes Bad Copies—So Far In Vitro," BioWorld Today 9 (61);1 (Apr. 1, 1998).
Linden et al., "The Recombination Signals for Adeno-Associated Virus Site-Specific Integration," Proc. Nat'l Acad. Sci. U.S.A. 93:7966-7972 (1996).

(Continued)

*Primary Examiner* — Quang Nguyen
(74) *Attorney, Agent, or Firm* — Nixon Peabody LLP; Mark J. FitzGerald

(57) ABSTRACT

This invention provides methods for obtaining targeted gene modification in vertebrate cells using parvoviral vectors, including adeno-associated virus (AAV). The parvoviral vectors used in the methods of the invention are capable of targeting a specific genetic modification to a preselected target locus in a cellular genome by homologous pairing.

20 Claims, 17 Drawing Sheets

(56) References Cited

OTHER PUBLICATIONS

Liu et al., "Type III Collagen is Crucial for Collagen I Fibrillogenesis and for Normal Cardiovascular Development," Proc. Nat'l. Acad. Sci. U.S.A. 94:1852-1856 (1997).
Maxwell et al., "Recombinant LuIII Autonomous Parvovirus as a Transducing Vector for Human Cells," Human Gene Ther. 4(4):441-450 (1993).
McCarty et al., "Analysis of Mutations in Adeno-Associated Virus Rep Protein In Vivo and In Vitro," J. Virol. 66 (7):4050-4057 (1992).
Miller et al., "Targeted Vectors for Gene Therapy," FASEB J. 9:190-199 (1995).
Moreadith et al., "Gene Targeting in Embryonic Stem Cells: The New Physiology and Metabolism," J. Mol. Med. 75:208-216 (1997).
Mullins et al., "Perspectives Series: Molecular Medicine in Genetically Engineered Animals," J. Clin. Invest. 98(11): S37-S40 (1996).
Ngo et al., "Computational Complexity, Protein Structure Prediction, and the Levinthal Paradox," Chapter 14 in The Protein Folding Problem and Tertiary Structure Prediction (Merz et al., eds. 1994).
Rudinger, "Characteristics of the Amino Acids as Components of a Peptide Hormone Sequence," in Peptide Hormones 1-7 (1976).
Rutledge et al., "Infectious Clones and Vectors Derived From Adeno-Associated Virus (AAV) Serotypes Other Than AAV Type 2," J. Virol. 72(1):309-319 (1998).
Seamark, "Progress and Emerging Problems in Livestock Transgenesis: A Summary Perspective," Reprod. Fertil. Dev. 6(5):653-657 (1994).
Sikorski et al., "Sightings: Homing Viruses," Science 280 (5371):1956 (1998).
Smithies et al., "Insertion of DNA Sequences Into the Human Chromosomal Beta-Globin Locus by Homologous Recombination," Nature 317:230-234 (1985).
Summerford and Samulski, "Membrane-Associated Heparan Sulfate Proteoglycan Is a Receptor for Adeno-Assocaited Virus Type 2 Virions," J. Virol. 72(2):1438-1445 (1998).
Verma et al., "Gene Therapy—Promises, Problems and Prospects," Nature 389:239-242 (1997).
Walsh et al., "Regulated High Level Expression of a Human Gamma-Globin Gene Introduced Into Erythroid Cells by an Adeno-Associated Virus Vector," Proc. Nat'l. Acad. Sci. U.S.A. 89:7257-7261 (1992).
Xiao et al., "Gene Therapy Vectors Based on Adeno-Associated Virus Type 1," J. Viol. 73(5):3994-4003 (1999).
Yang et al., "Mutational Analysis of the Adeno-Associated Virus rep Gene," J. Virol. 66(10):6058-6069 (1992).
Luo, F., et al. "Adeno-assocated virus 2-mediated transfer and fucntional expression of a gene encoding the human granulocyte-macrophage colony-stimulating factor," Blood, Journal of the American Society of Hematology (1993) Abstract No. 1196.
Zhou, S.Z., et al. "Adeno-associated virus 2-mediated gene transfer in hematopoietic progenitor cells in human umbilical cord blood," Blood, Journal of the American Society of Hematology (1993) Abstract No. 1197.
Wursthorn, et al. "Liver Directed AAV-Mediated Homologous Recombination is Independent of Serotype," American Society of Gene Therapy Meeting Abstracts (2007), Abstract No. 840.
Wursthhorn, et al. "In Vivo Correction of a Metabolic Liver Disease by AAV8-Mediated Homologous Recombination," American Society of Gene Therapy Meeting Abstracts (2007), Abstract No. 804.
Miller, et al. "Gene targeting in vivo by adeno-associated virus vectors," Nature Biotechnology, vol. 24, No. 8, pp. 1022-1026 (2006).
Chamberlain, et al. "Gene targeting in stem cells from individuals with osteogenesis imperfecta," Science, vol. 303, pp. 1198-1201, (2004).
Garofalo, et al. "Knocking out the bad allele," Gene Therapy, 11:1301-1302, (2004).
Sikorski, et al. "Sightings: Homing Viruses," Science, vol. 280, No. 5371, p. 1956, (1998).
Boyce, "Hit Squad—After years of target practice, gene therapy improves its aim," New Scientist, 2129:7, (1998).

Prockop, Targeting gene therapy for osteogenesis imperfecta, N Engl J Med, 350;22, pp. 2302-2304, (2004).
Vasileva, et al. "Precise hit: Adeno-associated virus in gene targeting," Nature Reviews, Microbiology, Published Online Oct. 2005.
Hendrie, et al. "Gene targeting with viral vectors," Molecular Therapy, vol. 12, No. 1, Jul. 2005.
Cummins, et al. "X-linked inhibitor of apoptosis protein (XIAP) is a nonredundant modulator of tumor necrosis factor-related apoptosis-inducing ligand (TRAIL)-mediated apoptosis in human cancer cells," Cancer Research, 64, pp. 3006-3008, (2004).
Li, M. et al. "Disruption of HAUSP gene stabilizes p53," Nature, 416, pp. 648-653, (2002).
Hirata, et al. "Efficient PRNP Gene Targeting in Bovine Fibroblasts by Adeno-Associated Virus Vectors," Cloning and Stem Cells, vol. 6, No. 1, pp. 31-36, (2004).
Flotte, T., et al. "Expression of the cystic fibrosis transmembrane conductance regulator froma novel adeno-associated virus promoter," The Journal of Biological Chemistry, vol. 268, No. 5, pp. 3781-3790, (1993).
Flotte, T., et al. "Stable in vivo expression of the cystic fibrosis transmembrane conductance regulator with an adeno-associated virus vector," Proc. Natl. Acad. Sci. vol. 90, pp. 10613-10617, (1993).
Hirata and Russell, "Design and packaging of adeno-associated virus gene targeting vectors," Journal of Virology, vol. 74, No. 10, pp. 4612-4620, (2000).
Liu, X., et al. "Targeted correction of single-base-pair mutations with adeno associated virus vectors under nonselective conditions," Journal of Virology, vol. 78, No. 8, pp. 4165-4175, (2004).
Ohi, et al. Construciton and replication of an adeno-associated virus expression vector that contains human β-globin cDNA, Gene, vol. 89, pp. 279-282, (1990).
Walsh, C., et al. "Phenotyppic correction of fanconi anemia in human hematopoictic cells with a recombinant adeno-associated virus vector," The Journal of Clinical Investigation, Inc., vol. 94, pp. 1440-1448, (1994).
Walsh, C., et al. "Regulated high level expression of a human g-globin gene introduced into erythroid cells by an adeno-associated virus vector," Proc. Natl. Acad. Sci. vol. 89, pp. 7257-7261, (1992).
Aguzzi et al., "Transgenic and Knock-out Mice: Models of Neurological Disease," *Brain Path*. 4:3-20 (1994).
Bernstein, "Have you used an adeno vector . . . lately?" *Nature Genetics*, 18:305-306 (Apr. 1998).
Bohenzky et al., "Sequence and Symmetry Requirements within the Internal Palindromic Sequences of the Adeno-Associated Virus Terminal Repeat," *Virology* 166:316-27 (1998).
Bradley, et al., "Modifying the Mouse Design and Desire," *Biotechnology* 10: 534-539 (1992).
Chíoríní et al., "Cloning of Adeno-Associated Virus Type 4 (AAV4) and Generation of Recombinant AAV4 Particles," *J. Virol*, 71: 6823-6833 (Sep. 1997).
Christensen et al., "A Novel Cellular Site-Specific DNA-Binding Protein Cooperates with the Viral NS1 Polypeptide to Initiate Parvoirus DNA Replication,"*J. Virol*. 71: 1405-1416 (Feb. 1997).
Corsini et al., "Symmetric-Strand Packaging of Recombinant Parvovirus LuIII Genomes That Retain Only the Terminal Regions," *J. Virol*. 69: 2692-2696 (Apr. 1995).
Costello et al., "The Mismatched Nucleotides in the 5'-Terminal Hairpin of Minute Virus of Mice are Required for Efficient Viral DNA Replication," *J. Virol*. 69: 7489-7496 (Dec. 1995).
Doetschman et al., "Establishment of Hamster Blastocyst-Derived Embryonic Stem (ES) Cells," *Dev. Biol*. 127:224-227 (1998).
DuPont et al., "Use of an Autonomous Parvovirus Vector for Selective Transfer of a Foreign Gene into Transformed Human Cells of Different Tissue Origins and Its Expression Therein," *J. Virol*. 68:1397-1406 (Mar. 1994).
Flotte and Carter, "Adeno-associated virus vectors for gene therapy," *Gene Therapy* 2: 357-362 (1995).
Graves and Moreadith, "Derivation and Characterization of Putative Pluripotential Embryonic Stem Cells From Preimplantation Rabbit Embryos,"*Mol. Reprod. Dev*. 36:424-433 (1993).
Hong et al., "Production of medakafish chimeras from a stable embryonic stem cell line," *Proc. Natl. Acad. Sci. USA* 95:3679-3684 (1998).

(56) References Cited

OTHER PUBLICATIONS

Iannaccone et al., "Pluripotent Embyronic Stem Cells from the Rat Are Capable of Producing Chimeras," *Dev, Biol.* 163:288-292 (1994).

Inoue, et al., "High-Fidelity Correction of Mutations at Multiple Chromosomal Positions by Adeno-Associated Virus Vectors," *J. Virol.* 73(9): 7376-7380 (Sep. 1999).

Kearns et al., "Recombinant adeno-associated virus (AAV-CFTR) vectors do not integrate in a site-specific fashion in an immortalized epithelial cell line," *Gene Therapy* 3: 748-755 (1996).

Mitani, et al., "Gene Targeting in Mouse Embryonic Stem Cells with an Adenoviral Vector," *Somatic Cell and Molecular Genetics*, 21(4):221-231 (1995).

Muramatsu et al., "Nucleotide sequencing and generation of an infectious clone of adeno-associated virus 3," *Virology* 221:208-17 (Jul. 1, 1996)(abstract only).

Russell, et al., "Human Gene Targeting by Viral Vectors," *Nature Genetics*, 18:325-330 (Apr. 1998).

Russell et al., "Transformation-Dependent Expression of Interleukin Genes Delivered by a Recombinant Parvovirus," *J. Virol.* 66: 2821-2828 (May 1992).

Schoonjans et al., "Pluripotential Rabbit Embryonic Stem (ES) Cells Are Capable of Forming Overt Coat Color Chimeras Following Injection Into Blastocyst," *Mol. Reprod. Dev.* 45:439-43 (1996).

Sukoyan et al., "Isolation and Cultivation of Blastocyst-Derived Stem Cell Lines from American Mink (*Mustela vison*)," *Mol. Reprod. Dev.* 33:418-31 (1992).

Thomson et al., "Isolation of a primate embryonic stem cell line," *Proc. Natl. Acad. Sci. USA* 92:7844-7848 (Aug. 1995).

Wakamastsu & Ozato, "Establishment of a pluripotent cell line derived from medaka (*Oryzias latipes*) blastula embryo," *Mol. Mar. Bio. Biotechnol.* 3:185-91 (1994).

Wang and Srivastava, "A Novel Terminus Resolution-Like Site in the Adeno-Associated Virus Type 2 Genome," *J. Virol.* 71:1140-1146 (Feb. 1997).

Wang et al., "Adeno-Associated Virus Type 2 DNA Replication In Vivo: Mutation Analyses of the D Sequence in Viral Inverted Terminal Repeats," *J. Virol.* 71:3077-3082 (Apr. 1997).

Ward and Berns, "Short Communication: Minimum Origin Requirements for Linear Duplex AAV DNA Replication in Vitro," *Virology* 209:692-05 (1995).

Weitzman et al., "Adeno-associated virus (AAV) Rep proteins mediate complex formation between AAV DNA and its integration site in human DNA,"*Proc. Natl. Acad. Sci. USA* 91:5808-5812 (Jun. 1994).

Wheeler, "Development and Validation of Swine Embryonic Stem Cells: a Review," *Reprod. Fertil. Dev.* 6:563-68 (1994).

Xiao et al., "A Novel 165-Base-Pair Terminal Repeat Sequence Is the Sole cis Requirements for the Adeno-Associated Virus Life Cycle," *J. Virol.* 71:941-948 (Feb. 1997).

Yanez, et al., "Therapeutic Gene Targeting," *Gene Therapy*, 5:149-159 (Feb. 1998).

Lebkowski, J.S. et al., Mol Cell Biol, 8:3986-3996 (1988). "Adeno Associated Virus: a Vector System for Efficient Introduction and Integration of DNA into a Variety of Mamallian Cell Types."

\* cited by examiner

Gene Correction in HSN039 Cells by AAV-SNO648

AP gene targeting vectors.

Vectors for *neo* gene correction.

AP gene correction in mutant fibroblasts.

β-*glucuronidase* genomic locus and vectors.

β-*gal* transgenes and vectors.

TARGETED GENE MODIFICATION BY PARVOVIRAL VECTORS

CROSS-REFERENCE TO RELATED APPLICATIONS

This application is a continuation application which claims benefit as applicable under 35 U.S.C. Sections 120, 121 or 365(c) of U.S. patent application Ser. No. 10/423,604 filed Apr. 24, 2003, now U.S. Pat. No. 7,972,856, which is a continuation application and claims benefit as applicable under 35 U.S.C. Sections 120, 121 or 365(c) of U.S. patent application Ser. No. 09/428,172 filed Oct. 27, 1999, now abandoned, which claims benefit under 35 U.S.C. §119(e) of U.S. Provisional Patent Application No. 60/106,191, filed Oct. 28, 1998, and is a continuation-in-part application which also claims priority benefit as applicable under 35 U.S.C. Sections 120, 121 or 365(c) to PCT Patent Application No. US98/07964, filed Apr. 20, 1998, which application designates the United States and claims priority benefit under 35 U.S.C. §119(e) to U.S. Provisional Patent Application No. 60/044,789, filed Apr. 24, 1997. Each of these applications is incorporated herein by reference for all purposes.

STATEMENT REGARDING FEDERALLY SPONSORED RESEARCH

This invention was made with government support under Grant Nos: P01HL53750 and HL03100, awarded by the National Institutes of Health. The Government has certain rights in the invention.

BACKGROUND OF THE INVENTION

1. Field of the Invention

This invention pertains to the field of targeted modification of cellular DNA in vertebrate cells by homologous pairing using parvoviral vectors, including vectors based on adeno-associated virus (AAV).

2. Background

Previously known methods for introducing defined mutations into mammalian chromosomes by gene targeting involve transfection, electroporation or microinjection (Smithies et al. (1985) *Nature* 317: 230-234; Thomas et al. (1986) *Cell* 44: 419-428). These methods, except for microinjection, produce homologous recombination events in only a small fraction of the total cell population, on the order of $10^{-6}$ in the case of mouse embryonic stem cells (Doetschman et al. (1987) *Nature* 330: 576-578; Thomas and Capecchi (1987) *Cell* 51: 503-512). Thus, the routine use of these methods requires preselection of transformed cells, making it difficult to apply the techniques to normal cells and in vivo applications.

Attempts to use transducing viral vectors to overcome these limitations and achieve chromosomal gene targeting experiments have been performed with retroviral and adenoviral vectors, but the results were not significantly better than can be obtained by transfection, with homologous recombination occurring in $10^{-5}$ to $10^{-6}$ cells (Ellis and Bernstein (1989) *Mol. Cell. Biol.* 9: 1621-1627; Wang and Taylor (1993) *Mol. Cell. Biol.* 13: 918-927).

Adeno-associated virus 2 (AAV) is a 4.7 kb single stranded DNA virus that has been developed as a transducing vector capable of integrating into mammalian chromosomes (Muzyczka (1992) *Curr. Top. Microbiol. Immunol.* 158: 97-129). Two thirds of integrated wild-type AAV proviruses are found at a specific human chromosome 19 site, 19q13-qter (Kotin et al. (1991) *Genomics* 10: 831-834; Kotin et al. (1990) *Proc. Nat'l. Acad. Sci. USA* 87: 2211-2215; Samulski et al. (1991) *EMBO J.* 10: 3941-3950). The site-specific integration event is a non-homologous recombination reaction that appears to be mediated by the viral Rep protein (Giraud et al. (1995) *J. Virol.* 69: 6917-6924; Linden et al. (1996) *Proc. Nat'l. Acad. Sci. USA* 93: 7966-7972). While this feature could prove useful in some applications, AAV vectors with deletions in the viral rep gene have not been found to integrate at this same locus (Russell et al. (1994) *Proc. Nat'l. Acad. Sci. USA* 91: 8915-8919; Walsh et al. (1992) *Proc. Nat'l. Acad. Sci. USA* 89: 7257-7261). Southern analysis of integrated rep AAV vector proviruses suggests that integration sites are random (Lebkowski et al. (1988) *Mol. Cell. Biol.* 8: 3988-3996; McLaughlin et al. (1988) *J. Virol.* 62: 1963-1973; Russell et al. (1994) supra.; Walsh et al. (1992) supra.) and sequencing of integrated vector junction fragments has confirmed that integration occurs by non-homologous recombination at a variety of chromosomal sites.

Although the development of integrating vectors based on eukaryotic viruses has made possible the efficient introduction of genes into mammalian chromosomes, there are many situations where it would be preferable to modify specific chromosomal sequences. Rather than, for example, introducing a corrected version of gene at a chromosomal location other than the native locus for the gene, one could correct the defective allele at the native locus. This ability could eliminate unwanted chromosomal genotypes and avoid position effects on gene expression. The need for such an ability to modify a preexisting locus is particularly acute in gene therapy, where mutant genes can have dominant effects and tissue-specific controls on expression are often critical.

Thus, a need exists for methods of obtaining specific genetic modification at selected target sites in vertebrate cellular genomes at high frequencies. The present invention fulfills this and other needs.

SUMMARY OF THE INVENTION

The present invention provides methods of producing a vertebrate cell that has a modification at a pre-selected target locus. The methods involve contacting the cell with a recombinant parvoviral vector that includes a) a targeting construct having a DNA sequence that is substantially identical to the target locus except for the modification being introduced, and b) all or part of at least one parvoviral ITR or a functional equivalent thereof. Upon entry of the vector into the cell, homologous pairing occurs between the targeting construct and the target locus, resulting in the modifications being introduced into the target locus. The modification can include one or more deletions, insertions, substitutions, or a combination thereof. The methods can be used for introducing a second modification at a second target locus by transducing a cell with a parvoviral vector that has a second targeting construct that is at least substantially identical to the second target locus except for the second modification. Additional target loci can be modified by transduction using parvoviral vectors that have appropriate targeting constructs. More than one targeting construct can be included on each parvoviral vector.

Also provided by the invention are vertebrate cells that contain specific genetic modifications at one or more preselected target loci that were introduced into the cells, or ancestors of the cells, by contacting the cells with a parvoviral vector that has a recombinant viral genome which includes a targeting construct that includes a DNA sequence which is substantially identical to the target locus except for the modification being introduced. These cells can be cultured in vitro, ex vivo, or can be part of an organism.

The invention also provides methods for introducing a modification of a target locus in a cell in a vertebrate by contacting a cell ex vivo with a recombinant parvoviral vector that includes a) a targeting construct having a DNA sequence that is substantially identical to the target locus except for the modification being introduced, and b) all or part of at least one parvoviral ITR or a functional equivalent thereof. The recombinant parvoviral vector is introduced into the cell, after which homologous pairing occurs between the targeting construct and the target locus resulting in the modifications being introduced into the cellular DNA at the target locus. The modified cell is then introduced into a vertebrate.

In another embodiment, the invention provides methods for making a modification of a target locus in a cell in a vertebrate by administering to the vertebrate a recombinant parvoviral vector. The parvoviral vectors used in these methods include a) a targeting construct having a DNA sequence that is substantially identical to the target locus except for the modification being introduced, and b) all or part of at least one parvoviral ITR or a functional equivalent thereof. The recombinant viral genome is introduced into the cell, after which homologous pairing occurs between the targeting construct and the target locus resulting in the modifications being introduced into the cellular DNA at the target locus.

The invention also provides methods of making an animal that includes cells that have a modification of a target locus of interest. The methods involve introducing into a cell from which an animal can be reconstituted a recombinant parvoviral vector that includes: a) a targeting construct which comprises a DNA sequence which is substantially identical to the target locus except for the modification being introduced; and b) all or a portion of at least one parvoviral ITR or a functional equivalent. Homologous pairing occurs between the targeting construct and the target locus resulting in the modification being introduced into the target locus. The cell and/or progeny of the cell is then allowed to develop into an embryo and brought to term. The resulting animals, which can be either transgenic or chimeric animals, are also part of the invention.

In other embodiments, the methods of the invention are used to obtain modified nuclei that are used in nuclear transplantation. These methods involve using the gene targeting methods of the invention to introduce a desired modification into a target locus in the genome of the cell that is to serve as the nucleus donor. The nucleus from a cell that has the desired modification is introduced into a second cell from which an animal can be reconstituted. This cell is then allowed to develop into an embryo and brought to term. Again, the resulting animals, which are either transgenic or chimeric, are also provided by the invention.

The invention also provides methods for introducing recombination signals into the genome of cells. These recombination signals, e.g., lox sites, can serve as substrates for recombinases that recognize the particular polynucleotide sequences (e.g., the Cre polypeptide). In these embodiments, the targeting construct includes a recombination signal that is flanked by polynucleotide sequences that are substantially identical to the target locus. Upon introduction of the targeting construct into the cell, homologous pairing occurs with the target locus, resulting in the recombination signal being introduced into the target locus.

Also provided by the invention are methods for enhancing the efficiency of gene targeting. In some embodiments, the recombinant parvoviral vector includes a targeting enhancer. Enhancers can include, for example, modifications to the polynucleotide such as an adduct, a pyrimidine dimer, a deletion of a sugar and/or base or other modification of the DNA backbone, and the like. Targeting enhancers can also include polypeptides that are capable of enhancing gene targeting, for example, recombination polypeptides, DNA repair enzymes, and the like. These can be included within a viral particle, for example.

Other methods provided by the invention for enhancing the efficiency of gene targeting involve treating a target cell with an agent that enhances targeting efficiency. These agents include, for example, one or more of a cell cycle modulator, a DNA repair modulator, a DNA recombination modulator, a modulator of chromatin packaging, an inhibitor of apoptosis, and a DNA methylation inhibitor.

The invention also provides methods for determining the efficacy of parvoviral vector-mediated gene targeting. These methods involve providing a cell having an integrated retroviral provirus that includes a defective reporter gene. The reporter gene is defective in that it has a first mutation that prevents expression of a reporter gene product having a detectable phenotype. The retroviral provirus serves as a target locus that is uniform from cell to cell. A recombinant parvoviral vector is then introduced into the cell. The recombinant parvoviral vector includes at least a polynucleotide subsequence of the reporter gene, wherein the polynucleotide subsequence overlaps the location of the first mutation but does not include the first mutation. The reporter gene subsequence present in the parvoviral vector does not encode a functional reporter gene product, due either to a second mutation which prevents expression of a reporter gene product having a detectable phenotype, or because the subsequence does not encode a full-length reporter gene product. Homologous pairing occurs between the polynucleotide subsequence and the reporter gene resulting in correction of the first mutation and expression of the reporter gene. The efficiency of gene targeting is then determined by detecting the presence or absence of the reporter gene product.

Additional embodiments of the invention provide methods to enrich for cells in which gene targeting at a target locus has occurred. These methods involve providing cells having: a) a reporter gene that comprises a first mutation which prevents expression of a reporter gene product having a detectable phenotype, and b) a target locus at which a modification is desired. Recombinant parvoviral vectors are introduced into these cells which have the following elements: a) a selection construct which includes a polynucleotide subsequence of the reporter gene, wherein the polynucleotide subsequence overlaps the location of the first mutation but does not include the first mutation, and comprises a second mutation which prevents expression of a reporter gene product having a detectable phenotype; and b) a targeting construct that includes a DNA sequence which is substantially identical to the target locus except for the modification being introduced. Next, cells are identified in which the reporter gene product is expressed. The cells that express the reporter gene product comprise a population of cells in which homologous pairing has occurred between the polynucleotide subsequence and the reporter gene resulting in correction of the first mutation and expression of the reporter gene. This population of cells is then screened to identify those in which homologous pairing has occurred between the targeting construct and the target locus resulting in the modification being introduced into the target locus.

DETAILED DESCRIPTION

Definitions

Figure 1A:
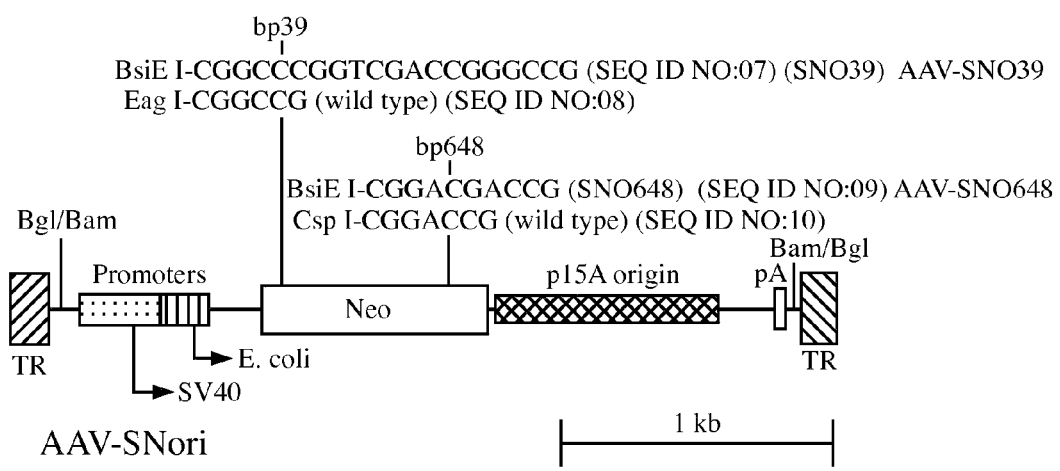
FIG. 1A is a diagram of the adeno-associated viral vector AAV-SNori, which is described in Example 1. This vector includes two AAV terminal repeats (TR), a bacterial gene encoding neomycin phosphotransferase (neo) under the control of an SV40 early promoter and a bacterial Tn5 promoter, a p15A plasmid replication origin, and a eukaryotic polyadenylation site. Also shown are the vectors AAV-SNO39 and AAV-SNO648, which contain mutations at by 39 and by 648 of the neo gene, respectively.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "cell line," as used herein, refers to individual cells, harvested cells, and cultures containing the cells, so long as they are derived from cells of the cell line referred to. A cell line is said to be "continuous," "immortal," or "stable" if the line remains viable over a prolonged time, typically at least about six months. To be considered a cell line, as used herein, the cells must remain viable for at least 50 passages. A "primary cell," or "normal cell," in contrast, refers to cells that do not remain viable over a prolonged time in culture.

The term "cis-active nucleic acid" refers to a nucleic acid subsequence that encodes or directs the biological activity of a nucleic acid sequence. For instance, cis-active nucleic acid includes nucleic acid subsequences necessary for modification of a nucleic acid sequence in a host chromosome, and origins of nucleic acid replication.

The term "constitutive promoter" refers to a promoter that is active under most environmental and developmental conditions.

The term "equivalent conditions" refers to the developmental, environmental, growth phase, and other conditions that can affect a cell and the expression of particular genes by the cell. For example, where inducibility of gene expression by a hormone is being examined, two cells are under equivalent conditions when the level of hormone is approximately the same for each cell. Similarly, where the cell cycle specificity of expression of a gene is under investigation, two cells are under equivalent conditions when the cells are at approximately the same stage of the cell cycle.

The term "exogenous" as used herein refers to a moiety that is added to a cell, either directly or by expression from a gene that is not present in wild-type cells. Included within this definition of "exogenous" are moieties that were added to a parent or earlier ancestor of a cell, and are present in the cell of interest as a result of being passed on from the parent cell. "Wild-type," in contrast, refers to cells that do not contain an exogenous moiety. "Exogenous DNA," as used herein, includes DNA sequences that have one or more deletions, point mutations, and/or insertions, or combinations thereof, compared to DNA sequences in the wild-type target cell, as well as to DNA sequences that are not present in the wild-type cell or viral genome.

The term "homologous pairing," as used herein, refers to the pairing that can occur between two nucleic acid sequences or subsequences that are complementary, or substantially complementary, to each other. Two sequences are substantially complementary to each other when one of the sequences is substantially identical to a nucleic acid that is complementary to the second sequence, as defined below.

The term "host cell" or "target cell" refers to a cell to be transduced with a specified vector. The cell is optionally selected from in vitro cells such as those derived from cell culture, ex vivo cells, such as those derived from an organism, and in vivo cells, such as those in an organism.

The term "identical" in the context of two nucleic acid or polypeptide sequences refers to the residues in the two sequences which are the same when aligned for maximum correspondence. Optimal alignment of sequences for comparison can be conducted, e.g., by the local homology algorithm of Smith and Waterman (1981) *Adv. Appl. Math.* 2: 482, by the homology alignment algorithm of Needleman and Wunsch (1970) *J. Mol. Biol.* 48:443, by the search for similarity method of Pearson and Lipman (1988) *Proc. Natl. Acad. Sci. USA* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by inspection.

An indication that two nucleic acid sequences are "substantially identical" is that the polypeptide which the first nucleic acid encodes is immunologically cross reactive with the polypeptide encoded by the second nucleic acid. Another indication that two nucleic acid sequences are substantially identical is that the two molecules and/or their complementary strands hybridize to each other under stringent conditions.

The phrase "hybridizing specifically to," refers to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Specific hybridization can also occur within a living cell.

An "inducible" promoter is a promoter which is under environmental or developmental regulation.

The term "labeled nucleic acid probe" refers to a nucleic acid probe that is bound, either covalently, through a linker, or through ionic, van der Waals or hydrogen "bonds" to a label such that the presence of the probe may be detected by detecting the presence of the label bound to the probe.

The term "label" refers to a moiety that is detectable by spectroscopic, radiological, photochemical, biochemical, immunochemical, or chemical means. For example, useful labels include $^{32}P$, $^{35}S$, fluorescent dyes, electron-dense reagents, enzymes (e.g., as commonly used in an ELISA), biotin, dioxigenin, green fluorescent protein (GFP), or haptens and proteins for which antisera or monoclonal antibodies are available.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "recombinant parvoviral vector genome" refers to a vector genome derived from a parvovirus that carries non-parvoviral DNA in addition to parvoviral viral DNA. The recombinant vector genome will typically include at least one targeting construct.

The term "replicating cell" refers to a cell that is passing through the cell cycle, including the S and M phases of DNA synthesis and mitosis.

The term "subsequence" in the context of a particular nucleic acid sequence refers to a region of the nucleic acid equal to or smaller than the specified nucleic acid.

A "target locus," as used herein, refers to a region of a cellular genome at which a genetic modification is desired. The target locus typically includes the specific nucleotides to be modified, as well as additional nucleotides on one or both sides of the modification sites.

A "targeting construct" refers to a DNA molecule that is present in the recombinant parvoviral vectors used in the methods of the invention and includes a region that is identical to, or substantially identical to, a region of the target locus, except for the modification or modifications that are to be introduced into the host cell genome at the target locus. The modification can be at either end of the targeting construct, or can be internal to the targeting construct. The modification can be one or more deletions, point mutations, and/or insertions, or combinations thereof, compared to DNA in the wild-type target cell.

The term "transduction" refers to the transfer of genetic material by infection of a recipient cell by a recombinant viral vector.

A cell that has received recombinant parvoviral vector DNA, thereby undergoing genetic modification, is referred to herein as a "transduced cell," a "transfected cell," a "modified cell," or a "recombinant cell," as are progeny and other descendants of such cells.

The term "transgenic cell" refers to a cell that includes a specific modification of the cell's chromosomal or other nucleic acids, which specific modification was introduced into the cell, or an ancestor of the cell. Such modifications can include one or more point mutations, deletions, insertions, or combinations thereof. When referring to an animal, the term "transgenic" means that the animal includes cells that are transgenic. An animal that is composed of both transgenic cells and non-transgenic cells is referred to herein as a "chimeric" animal.

The term "vector" refers to an agent for transferring a nucleic acid (or nucleic acids) to a host cell. A vector comprises a nucleic acid that includes the nucleic acid fragment to be transferred, and optionally comprises a viral capsid or other materials for facilitating entry of the nucleic acid into the host cell and/or replication of the vector in the host cell (e.g., reverse transcriptase or other enzymes which are packaged within the capsid, or as part of the capsid).

The term "viral vector" refers to a vector that comprises a viral nucleic acid and can also include a viral capsid and/or replication functions.

Description of the Preferred Embodiments

The present invention provides methods of producing a vertebrate cell that has a specific modification of a target locus. Genetically modified cells and animals produced using these methods are also provided. The methods involve introducing into the cell a recombinant parvoviral vector that is capable of targeting a genetic modification to a particular target locus by homologous pairing. The recombinant viral genomes of the parvoviral vectors used in the methods include a targeting construct that includes a DNA sequence that is substantially identical to the target locus except for the modification being introduced. Upon introduction of the recombinant viral genome into the cell, homologous pairing occurs between the targeting construct and the target locus, resulting in the introduction of the specific genetic modifications into the target locus.

The methods of the invention make possible precise modifications of the genome of a cell. This allows one to avoid undesired effects, such as disruption of a desirable gene by insertion of an exogenous gene, that can occur when other methods of modifying a genome are used. Moreover, one can achieve precise changes in a gene or a control region, for example, making possible the correction of an endogenous gene without having to insert a correct copy of the gene elsewhere in the genome. The methods avoid the frequently observed "position effect" in which the level of expression of an exogenous gene is highly dependent upon the location in a cell's genomic DNA at which the exogenous gene becomes integrated. The methods also make possible the modification of genes that are too large to be introduced into cells by other methods. Rather than having to introduce an entire copy of the gene that includes the desired modifications, one can use the methods of the invention to modify only a desired portion of the gene.

The methods of the invention use recombinant parvoviral vectors to insert DNA that includes desired genetic modifications into the vertebrate cells to be modified. A general introduction to human parvoviruses is found, e.g., in Pattison (1994) *Principles and Practice of Clinical Virology* (Chapter 23) Zuckerman et al. eds, John Wiley & Sons Ltd., and also in Berns (1991) "Parvoviridae and their Replication," In *Fundamental Virology*, Fields, Ed., Raven Press, New York, pp. 817-837, as well as references cited in each. The best characterized of the human parvoviruses are B19 and AAV, both of which are used as the basis for cell transduction vectors, e.g., for gene therapy. Other parvoviral vectors that can be used include, but are not limited to, the parvoviral vectors LuIII (Maxwell et al. (1993) *Human Gene Ther.* 4: 441-450) and minute virus of mice (mvm) (Russell et al. (1992) *J. Virol.* 66: 2821-2828.

In a preferred embodiment, the methods use a viral vector derived from an adeno-associated virus (AAV). AAVs are single-stranded, replication-defective DNA viruses with a 4.7 kb genome. Adeno-associated viruses are readily obtained, and their use as vectors for gene delivery was described in, for example, Muzyczka (1992) *Curr. Top. Microbiol. Immunol.* 158: 97-129, U.S. Pat. No. 4,797,368, and PCT Application WO 91/18088. Samulslci (1993) *Current Opinion in Genetic and Development* 3: 74-80 and the references cited therein provides an overview of the AAV life cycle. For a general review of AAVs and of the adenovirus or herpes helper functions see, Berns and Bohensky (1987) *Advances in Virus Research*, Academic Press., 32: 243-306. The genome of AAV is described in Srivastava et al. (1983) *J. Virol.*, 45: 555-564. Carter et al., U.S. Pat. No. 4,797,368, describe many of the relevant design considerations for constructing recombinant AAV vectors. See also, Carter WO 93/24641. Additional references describing AAV vectors include, for example, West et al. (1987) *Virology* 160: 38-47; Kotin (1994) *Human Gene Therapy* 5:793-801; and Muzyczka (1994) *J. Clin. Invest.* 94: 1351. Construction of recombinant AAV vectors is also described in a number of additional publications, including Lebkowski, U.S. Pat. No. 5,173,414; Lebkowski et al. (1988) *Mol. Cell. Biol.* 8: 3988-3996; Tratschin et al. (1985) *Mol. Cell. Biol.* 5(11):3251 3260; Tratschin et al. (1984) *Mol. Cell. Biol.*, 4: 2072-2081; Hermonat and Muzyczka (1984) *Proc. Nat'l. Acad. Sci. USA*, 81: 6466-6470; McLaughlin et al. (1988) and Samulski et al. (1989) *J. Virol.*, 63: 03822-3828. AAV is a defective human parvovirus, meaning that the virus is capable of replicating and forming virus particles only in cells that are also infected with a helper virus. To obtain integration of an AAV genome into a mammalian cell, the cell is infected with the AAV in the absence of a helper virus.

Parvoviral genomes have an inverted terminal repeat sequence (ITR) at each end. For use in the methods of the invention, the recombinant parvoviral vector genomes will typically have all or a portion of at least one of the ITRs or a functional equivalent, which is generally required for the parvoviral vectors to replicate and be packaged into parvovirus particles. A functional equivalent of an ITR is typically an inverted repeat which can form a hairpin structure. Both ITRs are often present in the recombinant parvoviral vector DNAs used in the methods. One can use the viral genomes in either single-stranded or double-stranded form.

The recombinant viral genomes of the parvoviral vectors used in the methods for genetically modifying vertebrate cells will include a targeting construct that, except for the desired modification, is identical to, or substantially identical to, the target locus at which genetic modification is desired. The targeting construct will generally include at least about 20 nucleotides, preferably at least about 100, and more preferably about 1000-5000 nucleotides or more, that are identical to, or substantially identical to, the nucleotide sequence of a corresponding region of the target locus. By "substantially identical" is meant that this portion of the targeting construct is at least about 80% identical; more preferably, at least about 90%, and most preferably at least about 99% identical to the corresponding region of the target locus.

The targeting construct will also include the genetic modification or modifications that are to be introduced into the target locus. The modifications can include one or more insertions, deletions, or point mutations, or combinations thereof, relative to the DNA sequence of the target locus. For example, to modify a target locus by introducing a point mutation, the targeting construct will include a DNA sequence that is at least substantially identical to the target locus except for the specific point mutation to be introduced. Upon introduction of the recombinant viral genome into the cell, homologous pairing occurs between the portions of the targeting construct that are substantially identical to the corresponding regions of the target locus, after which the DNA sequence of the mutation to be introduced that is present in the targeting construct replaces that of the target locus.

A targeting construct can have the genetic modifications at either end of, or within the region of the targeting construct that is identical to, or substantially identical to, the target locus. To delete a portion of a target locus, for example, the genetic modification will generally be within the targeting construct, being flanked by two regions of substantial identity to the target locus. Homologous pairing between the two regions of substantial identity and their corresponding regions of the target locus result in a portion of the sequence of the targeting construct, including the deletion, becoming incorporated into the target locus. Deletions can be precisely targeted to a desired location by this method. Similarly, genetic modifications that involve site-specific insertion of DNA sequences into the target locus can be made by use of a targeting construct that has the DNA sequence to be inserted flanked by or next to regions of substantial identity to the target locus. Homologous pairing between the targeting construct and the corresponding regions of the target locus is followed by incorporation of the insertion sequence into the target locus.

The methods of the invention can be used to introduce modifications at more than one target locus. For example, to introduce one or more modifications at a second target locus in a cellular genome, the cell can be contacted with a parvoviral vector that has a recombinant viral genome that has a targeting construct that is at least substantially identical to the second target locus, except for the desired modification or modifications. The targeting construct for the second target locus can be present in the same parvoviral vector as the targeting construct for the first target locus, or can be present in a second parvoviral vector. Where the first and second targeting constructs are present in different parvoviral vectors, the cells can be transduced with the vectors either sequentially or simultaneously. To obtain modifications at more than two target loci, this process is simply repeated as desired.

Structural genes, regulatory regions, and other sequences within the genomic or other DNA of a vertebrate cell are amenable to modification using the methods of the invention. For example, one can introduce specific changes within structural genes that can alter the gene product of the gene, or prevent the gene product from being expressed. A "structural gene" refers to the transcribed region of a gene, whether or not the gene is transcribed in a particular cell. In this embodiment, the recombinant viral genome can include a targeting construct that is identical to, or substantially identical to, the target locus, with the exception of the specific nucleotide changes to be introduced. Homologous pairing between the targeting construct and the target locus in the cellular DNA results in the modifications present in the targeting construct becoming incorporated into the target locus. Where the gene product is a polypeptide, for example, one can use the methods of the invention to obtain a gene that encodes a polypeptide having one or more specific amino acid substitutions, insertions, or deletions compared to the polypeptide encoded by the native gene. The methods allow one to replace a codon that specifies an amino acid that, when present, results in the polypeptide being inactive, or less active than desired, with a codon specifies an amino acid that restores normal activity to the polypeptide. Many genetic diseases that are characterized by one or more mutations that result in amino acid changes are correctable using the methods of the invention. As another example, a target region can be modified by substituting a codon that specifies a glycosylation site for a codon that encodes an amino acid that is not part of a glycosylation site, or vice versa. A protease cleavage site can be created or destroyed, as yet another example. A nonsense codon present in the target locus can be changed to a sense codon, or where disruption of the polypeptide is desired, one can introduce a nonsense mutation into the target locus. One can obtain a fusion protein by incorporating into the targeting construct an exogenous DNA that codes for the portion of the fusion protein that is to be joined to an endogenous protein; the exogenous DNA will be in the proper reading frame for translation of the fusion protein upon incorporation of the DNA sequence of the targeting construct into the cellular genome at the target locus.

Similarly, where the gene product is a nucleic acid, the methods can be used for modification of the gene products. RNA genes that can be modified using the methods of the invention include those from which are expressed tRNAs, ribosomal RNAs, ribozymes, telomerase subunits, and the like. Alternatively, the methods can be used to construct a gene for which the gene product consists of an endogenous nucleic acid linked to an exogenous nucleic acid. For example, an exogenous DNA that when transcribed produces a catalytic RNA can be linked to an endogenous gene. The RNA that is transcribed from this fusion gene can hybridize to endogenous nucleic acids that are substantially complementary to the endogenous portion of the fusion gene, after which the portion of the hybrid ribozyme that is expressed from the exogenous DNA can catalyze its usual reaction. Thus, the fusion gene obtained using the methods of the invention provides a means for targeting a ribozyme.

The methods of the invention also are useful for substituting, deleting or inserting nucleotides that make up regulatory regions that are involved in expressing a gene of interest. The altered regulatory region can change the expression of the gene by, for example, increasing or decreasing the level of expression of the gene compared to the level of expression under equivalent conditions in an unmodified cell. The modifications can, for example, result in expression of the gene under situations where the gene would not typically be expressed, or can prevent expression of a gene that normally would be expressed under particular circumstances. One can use the methods to insert a heterologous transcription control element, or modify an endogenous control element, such as a promoter, enhancer, transcription termination signal, at a location relative to the gene of interest that is appropriate for influencing expression of the gene. By replacing a constitutive promoter with an inducible promoter, for instance, one can tie expression of the gene to the presence or absence of a particular environmental or developmental stimulus. Similarly, regions that are involved in post-transcriptional modification, such as RNA splicing, polyadenylation, translation, as well as regions that code for amino acid sequences involved in post-translational modification, can be inserted, deleted, or modified. Examples of gene expression control elements that can be modified or replaced using the methods include, but are not limited to, response elements, promoters, enhancers, locus control regions, binding sites for transcription factors and other proteins, other transcription initiation signals, transcription elongation signals, introns, RNA stability sequences, transcription termination signals, polyadenylation sites, and splice sites. Expression of a gene can also be modulated by using the methods of the invention to introduce or destroy DNA methylation sites.

In one embodiment, the methods of the invention are used to obtain selective expression of a nucleic acid in a cell. Selective expression of a nucleic acid refers to the ability of the nucleic acid to be expressed in a desired cell type and/or under desired conditions (e.g., upon induction) but not to be substantially expressed in undesired cell types and/or under undesired conditions. Thus, the site and degree of expression of a particular nucleic acid sequence is regulated in a desired fashion. This is accomplished by, for example, introducing site-specific nucleotide substitutions, deletions, or insertions to create a nucleotide sequence that comprises a control element that is selectively expressed in the desired cell type and/or under desired conditions. This can be accomplished entirely by changing nucleotides that are already present in the target locus, or by incorporating into the target locus an exogenous DNA that includes a sequence that functions as all or part of a control element, or by a combination of these modifications.

For example, one can use the methods of the invention to introduce or disrupt a response element, which is a cis-acting nucleic acid sequence that interacts with a trans-activating or trans-repressing compound (usually a protein or a protein complexed with another material) to respectively stimulate or suppress transcription. Response elements that can be introduced or eliminated using the methods of the invention include cell-selective response elements, hormone receptor response elements, carbohydrate response elements, antibiotic response elements, and the like. A cell-selective response element is capable of being activated by a trans-activating regulatory element that is selectively produced in the cell type(s) of interest. The choice of cell-selective response element used in the methods depends upon whether the cell in which induction or repression of expression is desired produces the trans-activator that acts on the response element. For example, selective expression of a gene in pancreatic acinar cells, lens tissue, B cells, liver cells, and HIV-infected cells can be achieved by using the methods of the invention to introduce, respectively, an elastase I enhancer, a gamma crystallin gene response elements, an immunoglobulin heavy and/or light chain enhancer, a liver enhancer such as an α-1-antitrypsin or serum albumin enhancer, a chorionic gonadotropin α-chain or β-chain enhancer, an interleukin-2 (IL-2) enhancer, an IL-2 receptor enhancer, or a human immunodeficiency virus (HIV) response element such as the TAR site.

Hormone receptor response elements, which can be activated or repressed when a hormone, or a functional equivalent thereof, interacts with a cellular receptor for that hormone, can be introduced into a desired location using the methods of the invention. The hormone-receptor complex is internalized by the cell, where it selectively interacts with the appropriate hormone receptor response element (either directly or indirectly), thereby activating or repressing expression of genes operatively linked to the element. To obtain hormone-responsive induction or repression of expression, the methods are used to create a hormone response element upstream of a gene to be regulated. Expression of the gene will be regulated by the hormone in those cells that express receptors for the given hormone.

An antibiotic response element is regulated by the presence or absence of an antibiotic. For example, a tetracycline response element is responsive to tetracycline. Similarly, a carbohydrate response element is regulated by the presence or absence of certain carbohydrates or analogs thereof. Other response elements, as well as promoters, enhancers, and other regulatory regions, are well known to those of skill in the art. These can also be created or destroyed by use of the methods of the invention.

The methods of the invention can also be used to modify nucleic acid sequences that are involved in other cellular processes such as DNA replication (see, e.g., Kornberg and Baker, *DNA Replication*, $2^{nd}$ Ed., WH Freeman & Co., 1991), as well as matrix attached regions (see, e.g., Bode et al. (1996) *Crit. Rev. Eukaryot. Gene. Expr.* 6: 115-38; Boulikas (1993) *J. Cell. Biochem.* 52: 14-22), chromatin recombination hotspots (see, e.g., Smith (1994) *Experientia* 50: 234-41), and the like.

The invention also provides methods of introducing a recombination signal into a cell. In preferred embodiments, a specific recombinase enzyme is available which can catalyze recombination at the recombination signal. To introduce a recombination signal into a cellular genome, one or more recombination signals is included in the targeting construct, flanked by polynucleotide sequences that are at least substantially identical to the target locus. Homologous pairing followed by gene repair results in incorporation of the recombination signal(s) into the target locus.

One suitable recombination system is the Cre-lox system. In the Cre-lox system, the recombination sites are referred to as "lox sites" and the recombinase is referred to as "Cre." When lox sites are in parallel orientation (i.e., in the same direction), then Cre catalyzes a deletion of the polynucleotide sequence between the lox sites. When lox sites are in the opposite orientation, the Cre recombinase catalyzes an inversion of the intervening polynucleotide sequence. Thus, for example, one could use the methods of the invention to introduce two lox sites into target locus, oriented in opposite directions, and obtain inversion of the region between the lox sites by contacting the lox sites with the Cre polypeptide. If the two lox sites flank a promoter, for example, one could turn expression of a gene on or off simply by controlling the presence or absence of the Cre polypeptide. Such sites are also useful for introducing DNA that also includes a recombination signal at the location of the recombination signal in the target locus. In some embodiments, a gene encoding the Cre polypeptide is present in the cell, under the control of either a constitutive or an inducible promoter.

Several different lox sites are known, including lox511 (Hoess R. et al., *Nucleic Acids Res.* 14:2287-2300 (1986)), lox66, lox71, lox76, lox75, lox43, lox44 (Albert H. et al., *Plant J.* 7(4): 649-659 (1995)). This system works in various host cells, including mammalian cells (U.S. Pat. No. 4,959, 317; Sauer, B. et al., *Proc. Nat'l. Acad. Sci. USA* 85:5166-5170 (1988); Sauer, B. et al., *Nucleic Acids Res.* 17:147-161 (1989)); *Saccharomyces cerevisiae* (Sauer, B., *Mol Cell Biol.* 7:2087-2096 (1987)); and plants such as tobacco (Dale, E. et al., *Gene* 91:79-85 (1990)) and Arabdiopsis (Osborne, B. et al., *Plant J.* 7(4):687-701 (1995)) Use of the Cre-lox system in plants is also described in U.S. Pat. No. 5,527,695 and PCT application No. WO 93/0128.

Several other recombination systems are also suitable for use in the invention. These include, for example, the FLP/FRT system of yeast (Lyznik, L. A. et al., *Nucleic Acids Res.* 24(19):3784-9 (1996)), the Gin recombinase of phage Mu (Crisona, N. J. et al., *J. Mol. Biol.* 243(3):437-57 (1994)), the Pin recombinase of *E. coli* (see, e.g., Kutsukake K, et al., Gene 34(2-3):343-50 (1985)), the PinB, PinD and PinF from *Shigella* (Tominaga A et al., *J. Bacteriol.* 173(13):4079-87 (1991)), and the R/RS system of the pSRi plasmid (Araki, H. et al., *J. Mol. Biol.* 225(1):25-37 (1992)). Thus, recombinase systems are available from a large and increasing number of sources.

Through their use of parvoviral vectors to deliver the recombinant viral genome to a cell, the methods of the invention result in desired specific genetic modification events occurring at a much higher frequency than previously possible with other methods of site-specific modification of DNA in vertebrate cells. Desired modification frequencies of greater than 0.01% or greater are typically obtained using the methods; indeed, efficiencies greater than 0.1%, and even greater than 1% can be obtained using the methods. The efficiency of genetic modification depends in part on the multiplicity of infection (MOI; defined herein in units of vector particles per cell) used for the transduction, as well as the type of cell being transduced. In a typical embodiment, a MOI of about 1 to $10^{12}$ is used to transduce a cell obtained from a continuous cell line; more preferably the MOI is at least about $10^4$, and most preferably the MOI used in the methods of the invention is at least about $10^6$ vector particles per cell.

The methods are useful for introducing genetic modifications into any cells that are susceptible to transduction by the recombinant parvoviral vectors. Such cells can be obtained from many vertebrate species, including mammals, birds, reptiles, amphibians, fish, and the like. For example, cells from mammals such as human, cow, pig, goat, sheep, rodent, and the like can be modified using these methods. Cells that can be modified using the methods of the invention include brain, muscle, liver, lung, bone marrow, heart, neuron, gastrointestinal, kidney, spleen, and the like. Also amenable to genetic modification using the methods are germ cells, including ovum and sperm, fertilized egg cells, embryonic stem cells, and other cells that are capable of developing into an organism, or a part of an organism such as an organ. For example, one can use the methods of the invention to modify a cell that is to be a nucleus donor in a nuclear transplantation.

Both primary cells (also referred to herein as "normal cells") and cells obtained from a cell line are amenable to modification using the methods of the invention. Primary cells include cells that are obtained directly from an organism or that are present within an organism, and cells that are obtained from these sources and grown in culture, but are not capable of continuous (e.g., many generations) growth in culture. For example, primary fibroblast cells are considered primary cells. The methods are also useful for modifying the genomes of cells obtained from continuous, or immortalized, cell lines, including, for example, tumor cells and the like, as well as tumor cells obtained from organisms. Cells can be modified in vitro, ex vivo, or in vivo using the methods and vectors of the invention.

The methods are useful for modifying the genomes of vertebrate cell organelles, as well as nuclear genomes. For example, one can use the methods of the invention to modify a target locus in the mitochondrial genome of a cell by including in the recombinant viral genome a targeting construct that, except for the desired modification or modifications, is at least substantially identical to a target locus in the mitochondrial genome.

A. Preparing Vectors

The practice of this invention involves the construction of recombinant parvoviral vector genomes and, optionally, the packaging of these viral genomes into viral particles. Methods for achieving these ends are known in the art. A wide variety of cloning and in vitro amplification methods suitable for the construction of recombinant viral genomes are well-known to persons of skill Examples of these techniques and instructions sufficient to direct persons of skill through many cloning exercises are found in Berger and Kimmel, *Guide to Molecular Cloning Techniques, Methods in Enzymology* 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, NY, (Sambrook); *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel); Cashion et al., U.S. Pat. No. 5,017,478; and Carr, European Patent No. 0,246,864.

Examples of techniques sufficient to direct persons of skill through in vitro amplification methods are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3: 81-94; Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene* 4, 560; and Barringer et al. (1990) *Gene* 89: 117. Oligonucleotide synthesis, useful in cloning or amplifying nucleic acids, is typically carried out on commercially available solid phase oligonucleotide synthesis machines (Needham-VanDevanter et al. (1984) *Nucleic Acids Res.* 12:6159-6168) or chemically synthesized using the solid phase phosphoramidite triester method described by Beaucage et al. ((1981) *Tetrahedron Letts.* 22 (20): 1859-1862.

Typically, the recombinant viral genomes are initially constructed as plasmids using standard cloning techniques. The targeting constructs are inserted into the viral vectors, which include at least one of the two inverted terminal repeats or their functional equivalent. In some embodiments, the viral vector DNA is packaged into virions for use to infect the target cells. Viral vectors to be packaged can include in the viral genome DNA sequences necessary for replication and packaging of the recombinant viral genome into virions. In most embodiments, however, one or more of the replication and/or packaging polypeptides is provided by a producer cell line and/or a helper virus (e.g., adenovirus or herpesvirus). These helper functions include, for example, the Rep expression products, which are required for replicating the AAV genome (see, e.g., Muzyczka, N. (1992) *Current Topics in Microbiol. and Immunol.* 158: 97-129 and Kotin, R. M. (1994) *Human Gene Therapy* 5:793-801). The human herpesvirus 6 (HHV-6) rep gene can serve as a substitute for an AAV rep gene (Thomson et al. (1994) *Virology* 204: 304-311). The cap region, which encodes the capsid proteins VP1, VP2, and VP3, or functional homologues thereof, is also typically provided by a helper virus or producer cell line (Id.).

The recombinant viral genomes are grown as a plasmid and packaged into virions by standard methods. See, e.g., Muzyczka, supra., Russell et al. (1994) *Proc. Nat'l. Acad. Sci. USA* 91: 8915-8919, Alexander et al. (1996) *Human Gene Ther.* 7: 841-850; Koeberl et al. (1997) *Proc. Nat'l. Acad. Sci. USA* 94: 1426-1431; Samulski et al. (1989) *J. Virol.* 63: 3822-3828;

Tratschin et al. (1985) *Mol. Cell. Biol.* 5: 3251-3260; and Hermonat and Muzyczka (1984) *Proc. Nat'l. Acad. Sci. USA* 81: 6466-6470.

The recombinant viral genomes can be introduced into target cells by any of several methods. For example, as discussed above, one can package the viral genomes into parvoviral virions which are then used to infect the target cells. Alternatively, the recombinant viral genomes can be introduced into cells in an unpackaged form. For example, standard methods for introducing DNA into cells can be employed to introduce the viral genomes, such as by microinjection, transfection, electroporation, lipofection, lipid encapsulation, biolistics, and the like. The recombinant viral genomes can be incorporated into viruses other than parvoviruses (e.g., an inactivated adenovirus), or can be conjugated to other moieties for which a target cell has a receptor and/or a mechanism for cellular uptake (see, e.g., Gao et al. (1993) *Hum. Gene Ther.* 4: 17-24). The recombinant viral genomes can be introduced into either the nucleus or the cytoplasm of the target cells.

Methods of transfecting and expressing genes in vertebrate cells are known in the art. Transducing cells with viral vectors can involve, for example, incubating vectors with cells within the viral host range under conditions and concentrations necessary to cause transduction. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y.; and Muzyczka (1992) *Curr. Top. Microbiol. Immunol.* 158: 97-129, and references cited in each. The culture of cells, including cell lines and cultured cells from tissue samples is well known in the art. Freshney (*Culture of Animal Cells, a Manual of Basic Technique, Third edition* Wiley-Liss, New York (1994)) provides a general guide to the culture of cells.

The recombinant viral genomes and/or other components of a recombinant viral vector can be manipulated to improve targeting efficiency. These targeting enhancers can include, for example, adducts, pyrimidine dimers, and/or other DNA alterations that can induce cellular DNA synthesis, repair, and/or recombination systems, that are introduced into the viral genomes. Such alterations can include, modification of nucleotides in the viral DNA, such as elimination of one or more sugars, bases, and the like. For example, the parvoviral vectors can be treated with DNA damaging agents such as UV light, gamma irradiation, and alkylating agents. The modifications can be performed on the viral DNA in vitro or during or after packaging of the viral DNA into virions.

Other targeting enhancers that can be included are recombinogenic proteins. See, e.g., Pati et al. (1996) *Molecular Biol. of Cancer* 1:1; Sena and Zarling (1996) *Nature Genet.* 3: 365; Revet et al. (1993) *J. Mol. Biol.* 232: 779-791; Kowalczkowski & Zarling in *Gene Targeting* (CRC 1995, Ch. 7). The parvoviral vector nucleic acids can be associated with the recombinogenic proteins prior to being introduced into the cells, or the recombinogenic proteins can be introduced into the cells independently of the parvoviral vectors. In one presently preferred embodiment, the parvoviral vector is packaged in the presence of the recombinogenic protein, resulting in recombinogenic protein becoming packaged into the viral particles. The best-characterized recombinogenic protein is recA from *E. coli* and is available from Pharmacia (Piscataway N.J.). In addition to the wild-type protein, a number of mutant recA-like proteins have been identified (e.g., recA803). Further, many organisms have recA-like recombinases (e.g., Ogawa et al. (1993) *Cold Spring Harbor Symp. Quant. Biol.* 18: 567-576; Johnson and Symington (1995) *Mol. Cell. Biol.* 15: 4843-4850; Fugisawa et al. (1985) *Nucl. Acids Res.* 13: 7473; Hsieh et al. (1986) *Cell* 44: 885; Hsieh et al. (1989) *J. Biol. Chem.* 264: 5089; Fishel et al. (1988) *Proc. Nat'l. Acad. Sci. USA* 85: 3683; Cassuto et al. (1987) *Mol. Gen. Genet.* 208: 10; Ganea et al. (1987) *Mol. Cell. Biol.* 7: 3124; Moore et al. (1990) *J. Biol. Chem.* 19: 11108; Keene et al. (1984) *Nucl. Acids Res.* 12: 3057; Kimiec (1984) *Cold Spring Harbor Symp. Quant. Biol.* 48: 675; Kimeic (1986) *Cell* 44: 545; Kolodner et al. (1987) *Proc. Nat'l. Acad. Sci. USA* 84: 5560; Sugino et al. (1985) *Proc. Nat'l. Acad. Sci. USA* 85: 3683; Halbrook et al. (1989) *J. Biol. Chem.* 264: 21403; Eisen et al. (1988) *Proc. Nat'l. Acad. Sci. USA* 85: 25 7481; McCarthy et al. (1988) *Proc. Nat'l. Acad. Sci. USA* 85: 5854; Lowenhaupt et al. (1989) *J. Biol. Chem.* 264: 20568. Examples of such recombinase proteins include, for example, recA, recA803, uvsX (Roca (1990) *Crit. Rev. Biochem. Molec. Biol.* 25: 415), sep1 (Kolodner et al. (1987) *Proc. Nat'l. Acad. Sci. USA* 84: 5560; Tishkoff et al., *Mol. Cell. Biol.* 11: 2593), RuvC (Dunderdale et al. (1991) *Nature* 354: 506), DST2, KEMI, XRAU (Dykstra et al. (1991) *Mol. Cell. Biol.* 11: 2583), STPα/DST1 (Clark et al. (1991) *Mol. Cell. Biol.* 11: 2576), HPP-1 (Moore et al. (1991) *Proc. Nat'l. Acad. Sci. USA* 88: 9067), and other eukaryotic recombinases (Bishop et al. (1992) *Cell* 69: 439; Shinohara et al., *Cell* 69: 457). See also, PCT patent application PCT/US98/000852 (WO 98/31837).

The efficiency of gene targeting can also be improved by treating the host cell in conjunction with the introduction of the recombinant viral genome. For example, one can administer to the target cells an agent that affects the cell cycle. These agents include, for example, DNA synthesis inhibitors (e.g., hydroxyurea, aphidicolin), microtubule inhibitors (e.g., vincristine), and genotoxic agents (e.g., radiation, alkylators). Other agents that can improve the efficiency of gene targeting include those that affect DNA repair, DNA recombination, DNA synthesis, protein synthesis, and levels of receptors for AAV. Also of interest are agents that affect, chromatin packaging, gene silencing, DNA methylation, and the like, as less condensed DNA is more likely to be accessible for gene targeting. These agents include, for example, topoisomerase inhibitors such as Etoposide and camptothecin, and histone deacetylase inhibitors such as sodium butyrate and trichostatin A. Agents that inhibit apoptosis can also increase gene targeting by virtue of their ability to reduce the tendency of high concentrations of AAV to induce apoptosis. Suitable agents for these applications are described in, for example, U.S. Pat. No. 5,604,090, Russell et al. (1995) *Proc. Nat'l. Acad. Sci. USA* 92: 5719; Chen et al. (1997) *Proc. Nat'l. Acad. Sci. USA* 94: 5798; Alexander et al. (1994) *J. Virol.* 68: 8282; and Ferrari et al. ((1995) *J. Neurosci.* 15: 2857-66, (1998) *Mol. Cell. Biol.* 18: 6482-92, (1994) *EMBO J.* 13: 5922-8 (70:3227)).

The parvoviral vectors can also be targeted to a particular cell or tissue type by use of a virion or delivery vehicle that displays a molecule that binds to a moiety that is specific for a desired target cell. For example, an antibody that binds to a polypeptide found on cancer cells can be displayed on the delivery vehicle. In some embodiments, polynucleotides that encode a polypeptide which can specifically bind to the target cell are incorporated into a gene that encodes a parvoviral capsid protein. Upon packaging of the parvoviral vector genome, the modified capsid is displayed on the surface of the virion, thus allowing the virions to preferentially deliver the nucleic acid to the desired target cell. Modification of parvoviral capsid proteins for other purposes, as well as cell lines useful for expressing the genes that encode the modified proteins and methods of in vitro packaging using the modified capsid proteins, are described in U.S. Pat. No. 5,863,541, issued Jan. 26, 1999.

One can also improve gene targeting by using only one strand, either plus or minus, of the recombinant viral genomes. For example, use of a population of parvoviral vectors that each carry a plus strand, or that each carry a minus strand, can increase the efficiency of gene targeting. Alternatively, one can use a combination of plus and minus strands, each delivered by a different vector.

B. Identification of Cells Having Genetic Modifications

Because of the high frequencies with which specific genetic modifications occur using the methods of the invention, selection or screening for individual cells that include the desired modification is not necessary for many uses. Where it is desirable to identify cells that have incorporated a desired genetic modification, one can use techniques that are well known to those of skill in the art. For example, PCR and related methods (such as ligase chain reaction) are routinely used to detect specific changes in nucleic acids (see, Innis, supra, for a general description of PCR techniques). Hybridization analysis under conditions of appropriate stringency are also suitable for detecting specific genetic modifications. Many assay formats are appropriate, including those reviewed in Tijssen (1993) *Laboratory Techniques in Biochemistry and Molecular Biology—Hybridization with Nucleic Acid Probes, Parts I and II*, Elsevier, New York; and Choo (ed) (1994) *Methods In Molecular Biology* Volume 33—*In Situ Hybridization Protocols*, Humana Press Inc., New Jersey (see also, other books in the *Methods in Molecular Biology* series). A variety of automated solid-phase detection techniques are also appropriate. For instance, very large scale immobilized polymer arrays (VLSIPS™) are used for the detection of specific mutations in nucleic acids. See, Tijssen (supra), Fodor et al. (1991) *Science*, 251: 767-777 and Sheldon et al. (1993) *Clinical Chemistry* 39(4): 718-719.

These methods can be used to detect the specific genetic modifications themselves, or can be used to detect changes that result from the modification. For example, one can use hybridization or other methods to detect the presence or absence of a particular mRNA in a cell that has a modification in the promoter region.

One can also detect changes in the phenotype of the cells by other methods. For example, where a genetic modification results in a polypeptide being expressed in modified cells under conditions that an unmodified cell would not express the polypeptide, or vice versa, antibodies against the polypeptide can be used to detect expression. When the modified cells are in a vertebrate, the antibodies can be used to detect the presence or absence of the protein in the bloodstream or other tissue, for example. Where the genetic modification changes the structure of a polypeptide, one can obtain an antibody that recognizes the unmodified polypeptide but not the modified version, or vice versa. Methods of producing polyclonal and monoclonal antibodies are known to those of skill in the art, and many antibodies are available. See, e.g., Coligan (1991) *Current Protocols in Immunology* Wiley/Greene, N.Y.; and Harlow and Lane (1989) *Antibodies: A Laboratory Manual*, Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256: 495-497. Other suitable techniques for antibody preparation include selection of libraries of recombinant antibodies in phage or similar vectors. See, Huse et al. (1989) *Science* 246: 1275-1281 and Ward et al. (1989) *Nature* 341: 544-546. Vaughan et al. (1996) *Nature Biotechnology*, 14: 309-314 describe human antibodies with subnanomolar affinities isolated from a large 20 non-immunized phage display library. Chhabinath et al. describe a knowledge-based automated approach for antibody structure modeling ((1996) *Nature Biotechnology* 14: 323-328). Specific monoclonal and polyclonal antibodies and antisera will usually bind to their corresponding antigen with a $K_D$ of at least about 0.1 mM, more usually at least about 1 µM, preferably at least about 0.1 µM or better, and most typically and preferably, 0.01 µM or better. One can also detect the enzymatic activity (or loss thereof) of the modified enzyme.

Genetically modified cells can also be identified by use of a selectable or screenable marker that is incorporated into the cellular genome. A selectable marker can be a gene that codes for a protein necessary for the survival or growth of the cell, so only those host cells that contain the marker are capable of growth under selective conditions. For example, where the methods of the invention are used to introduce a genetic modification that places a gene that is required for cell growth under the control of an inducible promoter, cells that have incorporated the desired modification can be selected by growing the cells under selective conditions that also induce expression of the gene. Typical selection genes encode proteins that (a) confer resistance to antibiotics or other toxic substances, e.g., ganciclovir, neomycin, hygromycin, G418, methotrexate, etc.; (b) complement auxotrophic deficiencies, or (c) supply critical nutrients not available from complex media. The choice of the proper selectable marker will depend on the host cell, and appropriate markers for different hosts are well known in the art. A screenable marker is a gene that codes for a protein whose activity is easily detected, allowing cells expressing such a marker to be readily identified. Such markers include, for example, β-galactosidase, β-glucuronidase, and luciferase. Other markers include those that are identifiable by fluorescence-activated cell sorting. For example, a fluorescent protein such as green fluorescent protein (GFP) which permits separation of cells expressing the protein using a fluorescence activated cell sorter (FACS) machine, or using HOOK selection, available from Clontech). Alternatively, the marker can encode a polypeptide that is displayed on the cell surface and detectable by a fluorescence-labeled antibody.

C. In Vitro Uses

The methods of the invention are useful for constructing cells and cell lines that are useful for numerous purposes. Genetically modified cells can be used to produce a desired gene product at a greater level than otherwise produced by the cells, or a gene product that is modified from that otherwise produced. For example, one can modify a nonhuman cell gene that encodes a desired protein so that the amino acid sequence of the encoded protein corresponds to that of the human form of the protein. Or the amino acid sequence can be changed to make the protein more active, more stable, have a longer therapeutic half-life, have a different glycosylation pattern, and the like. The methods can be used to introduce a signal sequence at the amino terminus of a protein, which can facilitate purification of the protein by causing the cell to secrete a protein that is normally not secreted.

As another example, one can use the methods of the invention to modify cells to make them express a polypeptide that, for example, is involved in degradation of a toxic compound. If desired, expression can be made inducible by the presence of the toxic compound. Such cells can be used for bioremediation of toxic waste streams and for cleanup of contaminated sites.

Cells that have been modified using the methods of the invention are also useful for studying the effect of particular mutations. For example, one can disrupt expression of a particular gene and determine the effect of that mutation on growth and/or development of the cell, and the interactions of the cell with other cells. Genes suspected of involvement in disease, such as tumorigenesis (e.g., stimulators of angiogenesis) and other diseases, can be disrupted to determine the effect on disease development. Alternatively, expression of disease-related genes can be turned on or elevated and the effect evaluated.

Cells that are modified to express a particular gene under given conditions can be used to screen for compounds that are capable of inhibiting the expression of the gene. For instance, a cell can be modified to place a gene required for cell growth under the control of an inducible promoter. Test compounds are added to the growth medium along with the moiety that induces expression of the gene; cells in the presence of a test compound that inhibits the interaction between the inducing moiety and the inducible promoter will not grow. Thus, these cells provide a simple screening system for compounds that modulate gene expression.

The invention also provides libraries of targeted integrants. These libraries are particularly suitable for use in the screening assays described above, as well as for genetic analyses. Many other uses for the methods of the invention for introducing genetic mutations will be apparent to those of skill in the art.

D. Construction of Transgenic and Chimeric Animals

The invention also provides methods producing transgenic and chimeric animals, and transgenic and chimeric animals that are produced using these methods. A "chimeric animal" includes some cells that contain one or more genomic modifications introduced using the methods and other cells that do not contain the modification. A "transgenic animal," in contrast, is made up of cells that have all incorporated the specific modification or modifications. While a transgenic animal is capable of transmitting the modified target locus to its progeny, the ability of a chimeric animal to transmit the modification depends upon whether the modified target locus is present in the animal's germ cells. The modifications can include, for example, insertions, deletions, or substitutions of one or more nucleotides.

The methods of the invention are useful for producing transgenic and chimeric animals of most vertebrate species. Such species include, but are not limited to, nonhuman mammals, including rodents such as mice and rats, rabbits, ovines such as sheep and goats, porcines such as pigs, and bovines such as cattle and buffalo. Methods of obtaining transgenic animals are described in, for example, Puhler, A., Ed., *Genetic Engineering of Animals*, VCH Publ., 1993; Murphy and Carter, Eds., *Transgenesis Techniques: Principles and Protocols* (*Methods in Molecular Biology*, Vol. 18), 1993; and Pinkert, C A, Ed., *Transgenic Animal Technology: A Laboratory Handbook*, Academic Press, 1994. Transgenic fish having specific genetic modifications can also be made using the methods of the invention. See, e.g., Iyengar et al. (1996) *Transgenic Res.* 5: 147-166 for general methods of making transgenic fish.

One method of obtaining a transgenic or chimeric animal having specific modifications in its genome is to contact fertilized oocytes with a parvoviral vector that includes a targeting construct that has the desired modifications. For some animals, such as mice fertilization is performed in vivo and fertilized ova are surgically removed. In other animals, particularly bovines, it is preferably to remove ova from live or slaughterhouse animals and fertilize the ova in vitro. See DeBoer et al., WO 91/08216. In vitro fertilization permits the modifications to be introduced into substantially synchronous cells. Fertilized oocytes are then cultured in vitro until a pre-implantation embryo is obtained containing about 16-150 cells. The 16-32 cell stage of an embryo is described as a morula. Pre-implantation embryos containing more than 32 cells are termed blastocysts. These embryos show the development of a blastocoel cavity, typically at the 64 cell stage. Embryos of greater than one cell can also be modified by introducing the recombinant parvoviral genomes of the invention. If desired, the presence of a desired modification in the embryo cells can be detected by methods known to those of skill in the art. Methods for culturing fertilized oocytes to the pre-implantation stage are described by Gordon et al. (1984) *Methods Enzymol.* 101: 414; Hogan et al. *Manipulation of the Mouse Embryo: A Laboratory Manual*, C.S.H.L. N.Y. (1986) (mouse embryo); Hammer et al. (1985) *Nature* 315: 680 (rabbit and porcine embryos); Gandolfi et al. (1987) *J. Reprod. Fert.* 81: 23-28; Rexroad et al. (1988) *J. Anim. Sci.* 66: 947-953 (ovine embryos) and Eyestone et al. (1989) *J. Reprod. Fert.* 85: 715-720; Camous et al. (1984) *J. Reprod. Fert.* 72: 779-785; and Heyman et al. (1987) *Theriogenology* 27: 5968 (bovine embryos). Sometimes pre-implantation embryos are stored frozen for a period pending implantation. Pre-implantation embryos are transferred to an appropriate female resulting in the birth of a transgenic or chimeric animal depending upon the stage of development when the transgene is integrated. Chimeric mammals can be bred to form true germline transgenic animals.

Alternatively, the parvoviral vectors can be used to introduce specific genetic modifications into embryonic stem cells (ES). These cells are obtained from preimplantation embryos cultured in vitro. See, e.g., Hooper, M L, *Embryonal Stem Cells: Introducing Planned Changes into the Animal Germline* (Modern Genetics, v. 1), Intl. Pub. Distrib., Inc., 1993; Bradley et al. (1984) *Nature* 309, 255-258. Transformed ES cells are combined with blastocysts from a nonhuman animal. The ES cells colonize the 20 embryo and in some embryos form the germ line of the resulting chimeric animal. See Jaenisch, *Science,* 240: 1468-1474 (1988). Alternatively, ES cells or somatic cells that can reconstitute an organism ("somatic repopulating cells") can be used as a source of nuclei for transplantation into an enucleated fertilized oocyte giving rise to a transgenic mammal. See, e.g., Wilmut et al. (1997) *Nature* 385: 810-813.

For production of transgenic animals containing two or more modified target loci, parvoviral vectors containing two targeting constructs can be used, or more preferably two different parvoviral vectors, each containing a different targeting construct, are introduced simultaneously using the same procedure as for modifying a single target locus. Alternatively, each modification can be initially introduced into separate animals and then combined into the same genome by breeding the animals. Or a first transgenic animal is produced that includes one of the desired modifications, after which the second modification is introduced into fertilized ova or embryonic stem cells from that animal.

E. Ex Vivo Applications

The methods of the invention are useful for ex vivo applications, in which cells are removed from an organism, genetically modified using the methods, and reintroduced into an organism. In some applications genetically modified cultured cell lines will be introduced into an organism. The genetically modified cells can be introduced into the same organism from which the cells were originally obtained, or can be introduced into a different organism of the same or a different species. Ex vivo therapy is useful, for example, in treating genetic diseases such as hemophilia and certain types of thalassemia, as well as other diseases that are characterized by a defect in a cell that can be removed from the animal, modified using the methods of the invention, and reintroduced into the organism. The cells can be, for example, hematopoietic stem cells, which are derived from bone marrow or fetal cord blood, T-lymphocytes, B-lymphocytes, monocytes, liver cells, muscle cells, fibroblasts, stromal cells, skin cells, or stem cells. The cells can be cultured from a patient, or can be those stored in a cell bank (e.g., a blood bank). These methods are useful for treating humans, and also for veterinary purposes.

The modified cells are administered to the animal or patient at a rate determined by the $LD_{50}$ of modified cell type, and the side-effects of cell type at various concentrations, as applied to the mass and overall health of the patient. Administration can be accomplished via single or divided doses.

Animal models and clinical protocols for ex vivo gene therapy have been established for hematopoietic cells (Blaese et al. (1995) *Science* 270: 475-480; Kohn et al. (1995) *Nature Med.* 1: 1017-1023), liver cells (Grossman et al. (1994) *Nature Genet.* 6: 335-341), muscle cells (Bonham et al. (1996) *Human Gene Ther.* 7: 1423-1429), skin cells (Choate et al. (1996) *Nature Med.* 2: 1263-1267) and fibroblasts (Palmer et al. (1989) *Blood* 73: 438-445).

F. In Vivo Therapy

The methods of the invention are useful for correcting genetic defects in vivo. Muscular dystrophy is just one example of a genetic disease that is often the result of one or a few mutations that result in an abnormal polypeptide being expressed that is unable to carry out its function properly. The precise mutations for many variants of these and other genetic diseases are known to those of skill in the art, as are methods for identifying undesirable genetic mutations. Examples include, but are not limited to, Charcot-Marie-tooth disease, Coffin-Lowry syndrome, cystic fibrosis, fragile x syndrome, hemophilia, hereditary thrombotic predisposition (Factor V mutation) Huntington's disease, medium-chain acyl-coemzyme a dehydrogenase deficiency (mead), myotonic dystrophy, neurofibromatosis (nfl), sickle cell disease and globin chain variations, spinal muscular atrophy, spincocerebellar ataxia, α and β thalassemia, von Hippel-Lindau disease, and the like. Genetic diseases are reviewed in, for example, Shaw, D J (Ed.), *Molecular Genetics of Human Inherited Disease*, John Wiley & Sons, 1995; Davies and Read, *Molecular Basis of Inherited Disease*, $2^{nd}$ Edition, IRL Press, 1992. Human genetic diseases are treatable using the methods of the invention, as are those of other vertebrates. Non-genetic diseases can also be treated by manipulating genes. For example, one can modify a co-receptor for HIV so that the receptor is no longer able to bind to HIV particles.

The parvoviral vectors containing recombinant parvoviral genomes can be administered directly to the organism for modification of cells in vivo. Administration can be by any of the routes normally used for introducing viral vectors into ultimate contact with blood or tissue cells. The viral vectors used in the present inventive method are administered in any suitable manner, preferably with pharmaceutically acceptable carriers. Suitable methods of administering such viral vectors in the context of the present invention to a patient are available, and, although more than one route can be used to administer a particular viral vector, a particular route can often provide a more immediate and more effective reaction than another route.

Pharmaceutically acceptable carriers are determined in part by the particular viral vector being administered, as well as by the particular method used to administer the composition. Accordingly, there is a wide variety of suitable formulations of the pharmaceutical compositions of the present invention.

Formulations suitable for oral administration can consist of (a) liquid solutions, such as an effective amount of the vector dissolved in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the viral vector, carriers known in the art.

The viral vector, alone or in combination with other suitable components, can be made into aerosol formulations to be administered via inhalation. Because the bronchial passageways are the usual route of choice for certain viruses, corresponding vectors are appropriately administered by this method. Aerosol formulations can be placed into pressurized acceptable propellants, such as dichlorodifluoromethane, propane, nitrogen, and the like.

Suitable formulations for rectal administration include, for example, suppositories, which consist of the active viral vector with a suppository base. Suitable suppository bases include natural or synthetic triglycerides or paraffin hydrocarbons. In addition, it is also possible to use gelatin rectal capsules which consist of a combination of the viral vector with a base, including, for example, liquid triglyercides, polyethylene glycols, and paraffin hydrocarbons.

Formulations suitable for parenteral administration, such as, for example, by intraarticular (in the joints), intravenous, intramuscular, intradermal, intraperitoneal, intrathecal (in the cerebrospinal fluid), and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and in some embodiments, can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to a patient, in the context of the present invention should be sufficient to effect a beneficial therapeutic response in the patient over time. The dose will be determined by the efficacy of the particular viral vector employed and the condition of the patient or animal, as well as the body weight or surface area of the patient to be treated. The size of the dose also will be determined by the existence, nature, and extent of any adverse side-effects that accompany the administration of a particular vector or modified cell type in a particular patient or animal.

In determining the effective amount of the viral vector to be administered in the treatment or prophylaxis of a particular disease, the physician or veterinarian needs to evaluate circulating plasma levels, vector toxicities, and progression of the disease.

In the practice of this invention, the parvoviral vectors can be administered, for example, by aerosolization and inhalation, intravenous infusion, orally, topically, intramuscularly, intraperitoneally, intravesically or intrathecally. The preferred method of administration will often be intravenous or by inhalation, but the parvoviral vectors can be applied in a suitable vehicle for the local and topical treatment of virally-mediated conditions.

For administration, parvoviral vectors and genetically modified cell types of the present invention can be administered at a rate determined by the $LD_{50}$ of the parvoviral vectors, and the side-effects of the parvoviral vector or cell type at various concentrations, as applied to the mass and overall health of the patient. Administration can be accomplished via single or divided doses.

Protocols for in vivo gene therapy using adeno-associated viral vectors have been described for the brain (Alexander et al. (1996) *Human Gene Ther.* 7: 841-850), liver (Koeberl et al. (1997) *Proc. Nat'l. Acad. Sci. USA* 94: 1426-1431), lung (Flotte et al. (1993) *Proc. Nat'l. Acad. Sci. USA* 90: 10613-10617), and muscle (Xiao et al. (1996) *J. Virol.* 70: 8098-8108). These methods can be adapted to other target organs by those of skill in the art.

G. Systems for Assaying Efficiency of Gene Targeting

The invention also provides methods for determining the efficiency of parvoviral vector-mediated gene targeting. The methods involve using a retroviral vector to introduce into a target cell a mutant reporter gene that is subsequently corrected by gene targeting. The use of a retroviral vector to introduce the gene that is to be corrected has significant advantages over previously used assay systems. By placing the mutant reporter gene within a retroviral vector that becomes integrated into the target cell genome, the reporter gene becomes integrated into the cellular genome within a well-characterized chromosomal region (the integrated provirus). Because of this uniformity of the regions that surround the reporter gene, one can compare gene targeting efficiencies among a wide variety of cell types, including primary cells. Moreover, the retroviral vector proviruses can be introduced into cells as single copy targets by infecting the cells at a low multiplicity of infection. An additional advantage is that, one can use in the assays a polyclonal population of cells that contain target loci at thousands of different retroviral vector integration sites, thus taking into account variations in gene targeting rates due to position effects.

The reporter genes that are introduced into the target cells using the retroviral vectors are defective in that the detectable and/or selectable gene product of the reporter gene is not expressed, absent correction by gene targeting. For example, the reporter gene can be defective by virtue of a mutation in the coding region or in the promoter or other sequence that controls expression of the reporter gene. In presently preferred embodiments, the retroviral vectors include, in addition to the defective reporter gene, a selectable marker. Thus, one can select for cells that contain the integrated retroviral provirus. These cells are then used in the gene targeting assays.

Reporter genes that are suitable for use in the assays of the invention are known to those of skill in the art. Typically, the reporter genes encode a polypeptide that is directly detectable, e.g., a fluorescent polypeptide, or a polypeptide that is readily detectable through use of detection agents. For example, a reporter gene can encode an enzyme that, when present, converts a substrate into a readily detectable form. Alternatively, one can detect the reporter gene product through a detection agent that binds to the reporter gene product, for example, a labeled antibody. Suitable reporter genes include, but are not limited to, genes that encode β-glucuronidase (GUS, uidA) from *E. coli*, β-galactosidase, luciferase (LUC) from firefly, and green fluorescent protein (GFP) from jellyfish (see, e.g., Chalfie et al. (1994) *Science* 263:802-805; Crameri et al. (1996) *Nature Biotechnol.* 14: 315-319; Chalfie et al. (1995) *Photochem. Photobiol.* 62: 651-656; Olson et al. (1995) *J. Cell. Biol.* 130: 639-650) and related antigens, several of which are commercially available. In some embodiments, the reporter gene will encode a polypeptide that is expressed on the surface of the cells. One can then identify and enrich for those cells that have undergone successful gene targeting by, for example, flow cytometry-based cell sorting.

The reporter gene can also be a selectable marker that allows selection of modified cells that have undergone the desired gene targeting event. These genes can encode a gene product, such as a protein, necessary for the survival or growth of transformed host cells grown in a selective culture medium. Host cells that do not express the gene product of the selection gene will not survive in the culture medium. Typical selection genes encode proteins that confer resistance to antibiotics or other toxins, such as ampicillin, neomycin, kanamycin, chloramphenicol, or tetracycline. Examples of suitable coding sequences for selectable markers are: the neo gene which codes for the enzyme neomycin phosphotransferase which confers resistance to the antibiotics kanamycin, neomycin, and G418 (Beck et al. (1982) *Gene* 19:327); the hyg gene, which codes for the enzyme hygromycin phosphotransferase and confers resistance to the antibiotic hygromycin (Gritz and Davies (1983) *Gene* 25:179). Alternatively, selectable markers can encode proteins that complement auxotrophic deficiencies or supply critical nutrients not available from complex media. A number of selectable markers are known to those of skill in the art and are described for instance in Sambrook et al., supra.

The assays are conducted by introducing into the cells that contain the integrated retroviral provirus and associated defective reporter gene a recombinant parvoviral vector that includes the reporter gene that is defective due to a different mutation than that in the retroviral provirus. The defective reporter gene present in the parvoviral vector can be, for example, a full-length reporter gene that includes a mutation that prevents expression of an active reporter gene product (e.g., a mutation in the promoter, coding region, or other region that affects gene expression). Alternatively, the parvoviral vector can include only a subsequence of the reporter gene that is present in the retroviral provirus. In either case, the reporter gene present in the parvoviral vector overlaps the mutated region of the defective reporter gene in the retroviral provirus. The parvoviral vector reporter gene is mutated at a different location than the provirus reporter gene, so that the reporter gene product is produced only by those cells in which homologous pairing and gene repair has occurred between the two defective reporter genes.

The efficiency of gene targeting is then ascertained by determining the percentage of cells that express the reporter gene product.

In additional embodiments, the invention provides methods to enrich for cells in which gene targeting has occurred. These methods are based on the finding that a cell which undergoes gene targeting at one locus is more likely to undergo targeting at a second locus. Accordingly, two targeting constructs are introduced into cells. One targeting construct can correct a defective reporter gene that, upon correction, produces a readily detectable reporter gene product. The other targeting construct is directed to the gene of interest. The two targeting constructs can be present on the same parvoviral vector, but more commonly each will be contained on a separate parvoviral vector. After introduction of the targeting constructs into the cells, the cells are first screened or selected to identify those that express the reporter gene product. The resulting enriched cell populations are then screened to identify those cells in which the gene of interest has also undergone successful gene targeting.

The methods of enriching for target cells are useful for many applications. For example, germ cells, eggs, or other cells from which a transgenic organism can be reconstituted can be enriched for those cells that have undergone gene targeting. These cells are then screened to identify those that contain a desired alteration at the target locus of interest. Cells that have undergone the desired gene targeting event are then used to produce transgenic and/or chimeric animals.

EXAMPLES

The following examples are offered to illustrate, but not to limit the present invention.

Experimental procedures

A. Cell Culture

HeLa (Scherer et al. (1953) *J. Exp. Med.* 97: 695-709), HT-1080 (Rasheed et al. (1974) *Cancer* 33: 1027-33), and 293 (Graham et al. (1977) *J. Gen. Virol.* 36, 59-74) cells were cultured in Dulbecco's modified Eagle medium (DMEM) with 10% heat-inactivated (56° C. for 30 minutes) fetal bovine serum (HyClone, Logan, Utah), 1.25 µg/ml amphotericin, 100 U/ml of penicillin, and 100 µg/ml of streptomycin at 37° C. in a 10% $CO_2$ atmosphere. HT-1080 cells were maintained in HAT medium (DMEM containing 13.61 µg/ml hypoxanthine, 0.176 µg/ml aminopterin and 3.875 µg/ml thymidine prior to their use in transduction experiments to minimize the number of HPRT cells in the population.

HSNO39 cells were created by cotransfection of HeLa cells with a BamHI fragment containing the SV40 replication origin and promoter, mutant neo gene and p15A origin (the same fragment present in pASNO39; see FIG. 1A and below), and a BstYI fragment of pLHL containing the Moloney murine leukemia virus long terminal repeat promoter and hygromycin resistance gene. Transfected cells were selected for by growth in 0.2 mg/ml hygromycin (Calbiochem, San Diego, Calif.). HSNO39 cells were derived from a single hygromycin-resistant colony and shown by Southern analysis to contain 3 copies of the neo gene per cell. HSNO39 cells were cultured in medium containing 0.2 mg/ml hygromycin prior to their use in transduction experiments.

B. Plasmids

The plasmids pAAV/ad (Samulski et al. (1989) *J. Virol.* 63:3822-8), pACYC184 (Chang et al., (1978) *J. Bacteriol.* 134: 1141-56), pBluescript (Stratagene, La Jolla, Calif.), psub201 (Samulski et al. (1987) *J. Virol.* 61: 3096-101), pSV2neo (Southern and Berg (1982) *J. Mol. Appl. Genet.* 1: 327-41) and pTR (Ryan et al., (1996) *J. Virol.* 70: 1542-53) have been described. pLHL was a gift from A. D. Miller (Fred Hutchison Cancer Research Center, Seattle Wash.). pRepCap2 contains the XbaI fragment of psub201 containing the AAV2 rep and cap genes in the XbaI site of pBluescript. pASNori2 was constructed by inserting a BamHI-Esp3I neo fragment of pSV2neo containing a SspI-Bst11071 origin fragment from pACYC184 in the BstBI site (end-filled with Klenow fragment of DNA Polymerase I) downstream of the neo gene in to the Bg/II sites of the AAV vector backbone of pTR after attaching BamHI linkers to the pSV2neo Esp3I site. This same neo fragment was also used to construct the HSNO39 cell line. pASNO39 is identical to pASNori2 except for a SalI linker (5-CGGTCGACCG; SEQ ID NO:6) in the end-filled Eagl site. pASNO648 is identical to pASNori2 except for an end-filled and relegated Cspl site. pAHPe2/3 contains by 14, 057-17809 of the human HPRT locus (GenBank HUMHPRTB) in the BglII site of pTR as determined by DNA sequencing. pAHPe2/3X is identical to pAHPe2/3 except for an end-filled and relegated XhoI site. Both orientations of HPRT sequences relative to the pTR backbone were obtained and no differences were noted in the gene correction rates of the corresponding vectors. Human HPRT sequences were from the H&J lambda phage previously described (Patel et al. (1986) *Mol. Cell. Biol.* 6: 393-403).

C. Vector Production

AAV vector stocks were prepared as follows. 293 cells were plated at a density of $4 \times 10^6$ cells/dish in 24 dishes (10 cm). The next day each dish was infected with $5.6 \times 10^7$ plaque-forming units of adenovirus type 5 (ATCC VR-5) and two hours later cotransfected with 4 µg of vector plasmid and 16 µg of helper plasmid by the calcium phosphate method (Sambrook, supra.). After 3 days the cells and medium were harvested, freeze-thawed 3 times, clarified by centrifugation at 5800×g (5500 rpm) in a Sorvall HS4 rotor for 30 min. at 4° C., digested with 68 units/ml of micrococcal nuclease (Pharmacia, Piscataway, N.J.) at 37° C. for 1 hour, treated with 50 ng/ml of trypsin at 37° C. for 30 min., and centrifuged through 40% sucrose in phosphate buffered saline in a Beckman SW28 rotor at 27,000 rpm for 16 hours at 4° C. The pellets were resuspended in 8 ml of a 0.51 g/ml solution of CsCl and centrifuged in a Beckman SW41 rotor at 35,000 rpm for 20 hours at 4° C. The region of the gradient containing AAV virions was collected, dialyzed against DMEM through a 50,000 molecular weight cutoff membrane (Spectrum, Houston, Tex.) and concentrated by centrifugation in Centricon 100 filters (Amicon, Inc., Beverly, Mass.). The vector plasmids used were pASNori2 for AAV-SNori, pASNO648 for AAV-SNO648, pASNO39 for AAV-SNO39, pAHPe2/3 for AAV-HPe2/3 and pAHPe2/3X for AAV-HPe2/3X. The helper plasmids used were pAAV/Ad (Samulski et al. (1989) supra.) or pRepCap2, which produced equivalent stock titers.

The titer of each vector stock was determined by Southern blots of alkaline gels as follows. Ten µl stock dilutions were mixed with 2 µl of 10% SDS, heated to 100° C. for 10 minutes, electrophoresed through 1.2% alkaline agarose gels (Sambrook, supra.), blotted onto Hybon-N membranes (Amersham, Buckinghamshire, England) and probed for vector sequences. The amount of full-length linear vector DNA present in each sample was determined by comparison to standards present on the same gel using a Molecular Dynamics PhosphorImager 400S (Sunnyvale, Calif.), and the number of vector genomes per ml of stock calculated from this measurement. The same assay was used to locate vector particles on CsCl gradients by electrophoresing 10 µl of each gradient fraction. The number of intact vector genomes per ml of stock was the value used for vector particle numbers, which were typically $>10^{11}$/ml.

D. DNA Techniques

Enzymes were obtained from New England BioLabs, (Beverly, Mass.) Boehringer Mannheim, (Indianapolis, Ind.) or Stratagene (La Jolla, Calif.) and reactions were performed by using the manufacturers recommended conditions. Plasmid construction, DNA purification, Southern blot analysis and bacterial culture were performed by standard procedures (Sambrook et al., supra.). Plasmids were prepared by using Qiagen columns (Chatsworth, Calif.). Dye terminator cycle sequencing was carried out using the ABI PRISM sequencing kit (Perkin Elmer, Foster City, Calif.) and analyzed on an Applied Biosystems Inc. sequencer (Foster City, Calif.). Oligonucleotides were from Cruachem, Inc. (Dulles, Va.).

Integrated neo genes were rescued from transduced HSNO39 cells by digesting high molecular weight genomic DNA calf intestinal phosphatase to prevent ligation of free ends in the sample, heat inactivated, extracted with phenol and chloroform, and precipitated with ethanol. The resuspended DNA was digested with BamHI, extracted with phenol and chloroform and precipitated with ethanol. The resulting DNA fragments were resuspended, circularized with of T4 DNA ligase at 14° C. overnight and transferred to *E. coli* by electroporation or high efficiency chemical transformation. Bacterial colonies were selected for by growth on kanamycin plates.

Sequencing of the by 39 and by 648 mutations of corrected neo genes recovered as bacterial plasmids was performed with primers 9606D (dATGGCTTTCTTGCCGCCA) (SEQ ID NO:1) and 9607A (dATACGCTTGATCCGGCTAC) (SEQ ID NO:2) respectively. HPRT exon 3 sequences were amplified from high molecular weight genomic DNA by using a modification of a previously published procedure (Rossiter et al. (1991) "Detection of deletions and point mutations." In *PCR. A practical approach*, M. J. McPherson et al., eds. (Oxford, England: IRL Press), pp. 67-83) as follows. PCR was performed on 100 ng of genomic DNA in 20 µl reaction volume containing 2.1 picomoles of both 5 primer (dCCTTATGAAACATGAGGGCAAAGG) (SEQ ID NO:3) and 3 primer (TGTGACACAGGCAGACTGTGGATC) (SEQ ID NO:4), 6 mM $MgSO_4$, 1.25 mM each deoxynucleoside triphosphate, and 0.4 units Vent DNA Polymerase (New England Biolabs, Beverly, Mass.). The reaction was carried out in a PTC-200 thermocycler (MJ Research, Watertown, Mass.) with denaturation at 94° C. for 4.5 minutes, followed by 30 cycles of 94° C. for 30 seconds, 61° C. for 50 seconds and 72° C. for 2 minutes, then a final polymerization at 72° C. for 5 minutes. Six µl of the product was further amplified in a 100 µl volume under the same conditions for 20 cycles, and the PCR product was purified using a QIAquick kit (Qiagen, Chatsworth, Calif.) following the manufacturers protocol, and 75 ng of the purified product was used for DNA sequencing with the primer dACCTACTGTTGCCACTA (SEQ ID NO:5).

E. Gene Targeting Assays

Standard transduction experiments were performed by plating $5×10^3$ or $1×10^4$ HSNO39 cells/well respectively into 96 (Nunc, Naperville, Ill.) or 48 (Costar, Cambridge, Mass.) well plates or $2×10^4$ HT-1080 cells into 48 well plates on day 1. On day 2, the medium was changed and vector stock (prepared in DMEM) was added to the well. The MOI was calculated assuming one cell doubling since the original plating. On day 3, each well was treated with trypsin, and the cells were plated into 10 cm dishes. On day 4, the assays differed for each cell line.

For neo gene correction experiments, 90%, 9.5% and 0.5% of the cells from each well were plated into different dishes. On day 4, G418 (1 mg/ml active compound) was added to the 90% and 9.5% dishes and selection was continued for 10-12 days with medium changes every 3-4 days. G418 was not added to the 0.5% dishes which served as a control for the total number of colony-forming units (CFU) from each original well. The colonies present in each dish were counted after staining with Coomassie brilliant blue G. The neo gene correction rate was calculated as the number of G418-resistant CFU/total CFU for each original well.

For HPRT experiments, all the cells from each well were cultured without selection for 10-14 days after being plated into 10 cm dishes on day 3, to allow for elimination of existing HPRT protein in HPRT cells. No significant differences were noted in HPRT mutation rates after 10 day or 14 day culture periods. The medium was changed every 3-4 days and when dishes became too dense the cells were treated with trypsin and dilutions were plated into new dishes. After this phenotypic expression period, $10^5$, $10^4$ and $10^2$ cells of each culture were plated into new 10 cm dishes, and the following day 6TG (5 µg/ml) was added to the $10^5$ and $10^4$ cell dishes. 6TG selection was not applied to the $10^2$ cell dishes as these were used to calculate plating efficiencies. The cells were cultured for 10 additional days, stained with Coomassie brilliant blue G, and the surviving colonies were counted. The percent of 6TG-resistant CFU was determined after correcting for plating efficiencies.

Example 1

Correction of Mutant Neo Genes Using Adeno-Associated Viral Vectors

This Example demonstrates that vectors based on adeno-associated virus (AAV) can efficiently modify specific chromosomal target sequences in human cells.

We used the selectable neomycin phosphotransferase gene (neo) as a marker to study gene correction by transduction. The vectors constructed for these experiments were based on the AAV shuttle vector AAV-SNori (FIG. 1A), which contains the neo gene under the control of both the bacterial Tn5 promoter and SV40 early promoters, and the p15A plasmid replication origin, which supports stable replication in *Escherichia coli* (Cozzarelli et al. (1968) *Proc. Nat'l. Acad. Sci. USA* 60: 992-999). The AAV2 terminal repeats flank these internal sequences and contain all the cis-acting sequences required for replication and packaging of the vector genome (McLaughlin et al. 15 (1988) *J. Virol.* 62: 1963-1973; Samulski et al., supra.). Mammalian cells transduced by AAV-SNori are resistant to G418, and the integrated proviruses can be recovered as bacterial plasmids expressing kanamycin resistance. Mutations were introduced into the AAV-SNori vector at by 39 (a 14 nucleotide insertion) and by 648 (a 3 nucleotide insertion) of the neo gene (bp 1 being the translation start codon), to generate the vectors AAV-SNO39 and AAV-SNO648. Both mutations disrupt neo gene function, but gene correction between the two mutant genes can regenerate a functional gene and confer G418 resistance.

HeLa cells were used as a model human system to study gene correction by AAV vectors. A HeLa cell line containing integrated copies of the internal portion of the AAV-SNO39 genome (lacking the terminal repeats) was created by cotransfection of this fragment with a hygromycin selectable marker (see Experimental Procedures). Several hygromycin-resistant clones were isolated and screened for the presence the mutant neo gene cassette by Southern analysis. One cell line, designated HSNO39, appeared to contain 3 intact copies per cell of the neo cassette integrated at different locations and was chosen for further experiments.

A. Frequency of Neo Gene Correction

HSNO39 cells were infected with AAV-SNO648 vector stocks, treated with trypsin and plated at different dilutions on the following day, then selected in G418 two days after infection. Dilutions were also grown without selection to determine the total number of colony-forming units in the sample.

Correction of the mutant chromosomal neo genes by incoming vector genomes was measured as the fraction of colonies resistant to G418. As shown in Table 1, approximately 0.1% of HSNO39 cells were resistant to G418 after infection with AAV-SNO648. This represents a minimal neo gene correction rate as some cells could contain silenced genes with inadequate expression levels. Infection of HeLa cells with AAV-SNO648 did not produce G418-resistant colonies, demonstrating that reversion of the by 648 mutation in the vector did not occur at detectable rates. Similarly, G418-resistant colonies were not detected in uninfected HSNO39 cells or HSNO39 cells infected with AAV-SNO39, showing that reversion of the chromosomal by 39 mutation did not occur. About 0.6% of HeLa cells were resistant to G418 after transduction with the AAV-SNori vector, which contains a functional neo gene and can integrate at random chromosomal locations by non-homologous recombination. Thus the neo gene correction rate was about 5-fold lower than the random vector integration rate of a similar vector.

TABLE 1

Neo Gene Correction

| Cell Line | Vector/Plasmic: 1 | MOI | Fraction G418R |
|---|---|---|---|
| HSNO39 | none | — | $<5.3 \times 10-5$ |
| " | " | — | $<4.3 \times 1\ OT5$ |
| " | " | — | $<4.3 \times 105$ |
| " | " | — | $<1.4 \times 10-5$ |
| HSNO39 | AAV-SNO648 | 40,000 | $9.6 \times 104$ |
| " | " | 40,000 | $6.7 \times 10-4$ |
| " | " | 400,000 | $2.0 \times 10-3$ |
| " | " | 400,000 | $1.4 \times 10-3$ |
| HeLa | AAV-SNO648 | 40,000 | $<6.0 \times 10-5$ |
| " | " | 40,000 | $<5.7 \times 10-5$ |
| " | " | 400,000 | $<6.8 \times 10-5$ |
| " | " | 400,000 | $<6.6 \times 10-5$ |
| HSNO39 | AAV-SNO39 | 375,000 | $<6.3 \times 10-5$ |
| | | 1,500,000 | $<6.6 \times 10-5$ |
| HeLa | AAV-SNori | 100,000 | $7.3 \times 10-3$ |
| " | " | 100,000 | $5.3 \times 10-3$ |

B. Structure of the Chromosomal Neo Genes

Figure 1B:
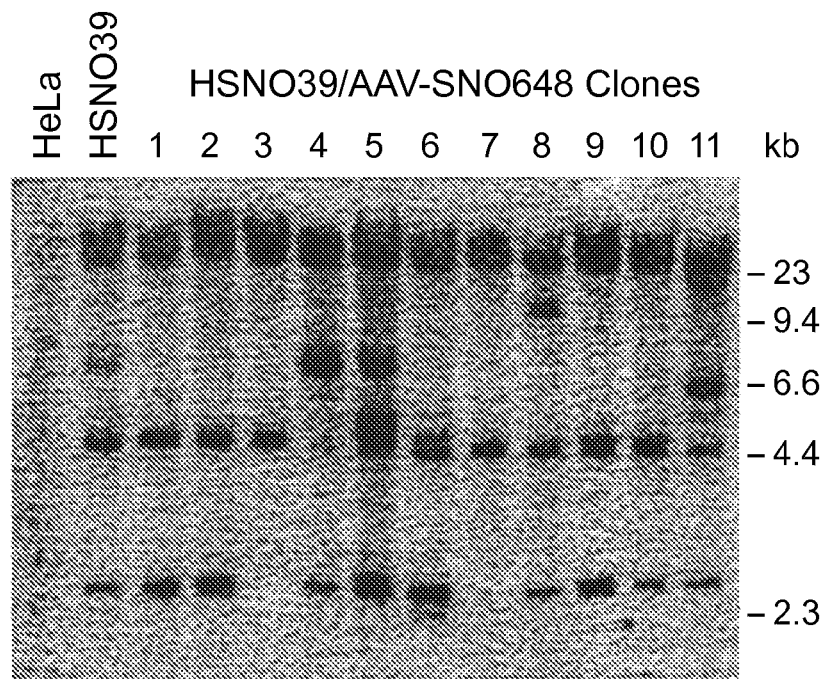
FIG. 1B is an autoradiogram which shows the results of a Southern blot analysis of BamHI-digested genomic DNA from G418-resistant HeLa cell clones that had been modified as described in Example 1. The lane captioned "HeLa" shows hybridization of a neo gene probe to genomic DNA from unmodified HeLa cells, the lane captioned "HSNO39" shows hybridization of the probe to genomic DNA from HSNO39 cells that contain three copies of a plasmid that contained the internal portion of AAV-SNO39, and lanes 1-11 show hybridization of the probe to eleven different clones obtained by modifying HSNO39 cells using the parvoviral vector AAV-SNO648.

Several G418-resistant colonies obtained by infecting HSNO39 cells with AAV-SNO648 were isolated, expanded to approximately $2\times10^7$ cells, and analyzed by Southern blots. After digestion with BamHI, genomic DNA from the parental HSNO39 cells contained 3 major neo-hybridizing bands of 2.7, 5.0 and >20 kb, representing the three integrated copies of the neo gene cassette (FIG. 1B). A 2.7 kb BamHI neo fragment was used to generate the HSNO39 line by cotransfection. A faint 8.0 kb band was also observed at less than one copy per cell, and may be due to methylation or mutation at one of the BamHI sites in a subset of HSNO39 cells. Four out of eleven HSNO39/AAV-SNO648 G418-resistant clones (1, 2, 9 and 10) contained the same 3 major bands as the parental line, with no additional fragments. The 8.0 kb band of clones 4 and 5 could represent the faint band of the same size in the parental line. New bands were observed in 4 of the clones, suggesting that random vector integration had also occurred in a subset of cells exposed to the vector. Three clones were missing bands present in the parental line (3, 4 and 7), which can be explained by modification of a BamHI site rather than rearranged neo cassettes, as no novel bands were observed in these clones. Homology between the vector and chromosomal neo cassettes extends up to the BamHI site, so modification of the chromosomal sequence at this site by vector DNA could have destroyed the site. These results demonstrate that the majority of G418-resistant clones isolated contained at least one corrected neo gene without additional rearrangements due to vector integration.

C. Sequence of the Corrected Neo Genes

To assess the fidelity of the gene correction process we recovered several corrected neo genes in bacterial plasmids and sequenced the relevant regions. The neo gene cassette present in HSNO39 cells and the AAV-SNO648 vector can replicate and confer kanamycin resistance in *E. coli* (FIG. 1A), allowing us to recover corrected neo genes as bacterial plasmids. Chromosomal DNA from the G418-resistant HSNO39/AAV-SNO648 clones shown in FIG. 1B was digested with BamHI, circularized with DNA ligase, and transferred to bacteria that were then selected for kanamycin resistance. As shown in Table 2, corrected neo genes were recovered as bacterial plasmids from 7/11 clones. It is possible that more persistent attempts to recover plasmids from the remaining 4 clones would also have been successful. Plasmids isolated from these bacteria were digested with BamHI and only those with a unique site were considered correct. A 2.7 kb plasmid was recovered from each of the seven clones that by restriction digestion appeared to be a circularized BamHI fragment identical to that used to produce the HSNO39 line, except for the absence of the by 39 mutation. A second 20 kb plasmid was also recovered from clone 11, which appeared to correspond to the high molecular weight band observed on Southern blots. Apparently at least two of the neo genes present in this cell line had been corrected. The recovered plasmids contained wild type neo genes based on digestion with BsiEI, which can identify the by 39 and by 648 mutations (see FIG. 1A).

TABLE 2

Rescue of Corrected Neo Genes

| Cell Line | Southern Results | KanR Colonies Recovered | Fraction Correct | Plasmid Sizes |
|---|---|---|---|---|
| HSNO39 | 2.7, 5.0, (8.0), >20 kb | 0 | — | — |
| Clone 1 | no change | 14 | 11/12 | 2.7 kb |
| Clone 2 | no change | 7 | 6/6 | 2.7 kb |
| Clone 3 | 02.7 kb | 0 | — | — |
| Clone 4 | 05.0 kb | 0 | — | — |
| Clone 5 | +5.5 kb | 7 | 6/7 | 2.7 kb |
| Clone 6 | +(2.4, 5.2) kb | 3 | 2/3 | 2.7 kb |
| Clone 7 | 02.7 kb | 0 | — | — |
| Clone 8 | +18 kb | 6 | 5/6 | 2.7 kb |
| Clone 9 | no change | 2 | 2/2 | 2.7 kb |
| Clone 10 | no change | 0 | — | — |
| Clone 11 | +6.6 kb | 4 | 4/4 | 2.7, 20 kb |

We sequenced the regions surrounding the by 39 and by 648 mutations of each recovered plasmid. More than 200 by of sequence was obtained from each region and in all cases the sequence corresponded exactly to that of the wild-type neo gene. Thus the gene correction process led to an accurate deletion of the 14 nucleotide insertion present at the chromosomal by 39 mutation, without additional genetic changes and without insertion of the by 648 mutation present in the vector. However, because our assay required the presence of a functional neo gene, any additional mutations created during the targeting event that disrupted neo gene function would have been excluded from our analysis.

Example 2

Modification of the Human HPRT Gene by AAV Vectors

We also studied gene correction by AAV vectors at the human hypoxanthine phosphoribosyltransferase locus (HPRT). The HPRT gene is frequently used to study mutation because HPRT cells can be selected for by growth in the presence of 6-thioguanine (6TG), so mutagenesis at the single copy X-linked locus can be measured in diploid male cells. We used HT-1080 human fibrosarcoma cells to study gene targeting at the HPRT gene because this cell line has a pseudodiploid male karyotype (Rasheed et al. (1974) *Cancer* 33: 1027-1033) and has been used previously in HPRT gene targeting experiments (Pikaart et al. (1992) *Mol. Cell. Biol.* 12: 5785-92; Zheng et al. (1991) *Proc. Nat'l. Acad. Sci. USA* 88: 8067-71).

Figure 2A:
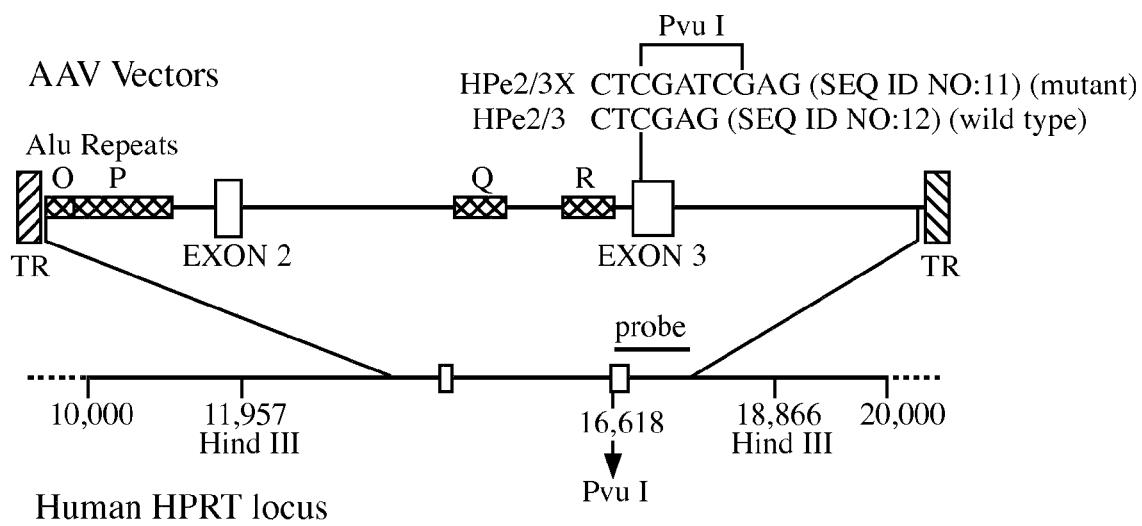
FIG. 2A is a diagram of the human HPRT locus, as well as the AAV vectors HPe2/3 and HPe2/3X, which were used to modify the human HPRT locus. In addition to the indicated portion of the HPRT gene, these vectors, which are described in Example 2, contain two AAV terminal repeats (TR), and four Alu repeats designated 0, P, Q, and R.
Figure 3:
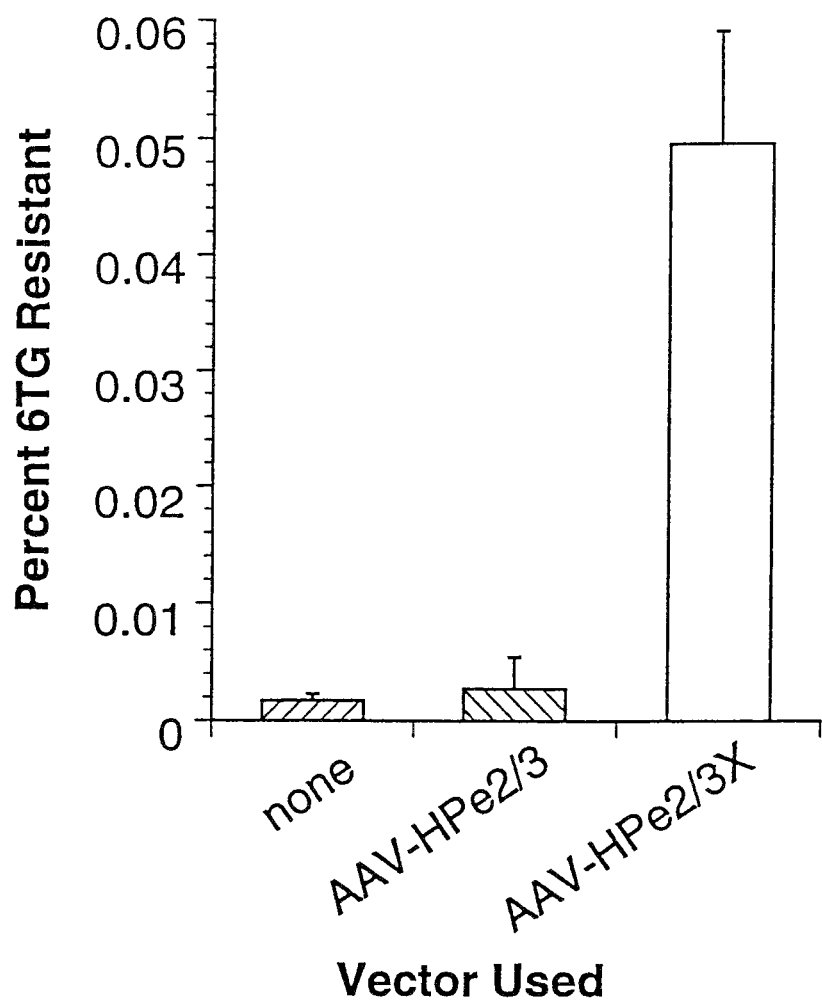
FIG. 3 shows the results of an experiment, described in Example 2, in which AAV vectors AAV-HPe2/3 and AAV-HPe2/3X were used to modify the HPRT locus in HT-1080 cells. The percent of 6TG-resistant cells obtained is shown.

AAV vectors containing a region of the human HPRT locus encompassing exons 2 and 3 were used to introduce a specific mutation into the HPRT gene of HT-1080 cells (FIG. 2A). The AAV-HPe2/3 vector contains wild type genomic sequence, while the AAV-HPe2/3X vector contains a 4 nucleotide insertion in exon 3, which causes a frameshift in the HPRT coding sequence. HT-1080 cells were infected with both vectors and selected for 6TG resistance after culturing the cells for a period without selection to allow for elimination of existing HPRT protein (see Experimental Procedures). As shown in FIG. 3, about 1/2000 HT-1080 cells infected with the mutant AAV-HPe2/3X vector were 6TG-resistant. This represents the minimum HPRT gene modification frequency, as HT-1080 cells are not uniformly diploid and could contain additional X chromosomes (Rasheed et al., supra.). The AAV-HPe2/3X vector targeting frequency was about 30 fold above the background mutation rate. Infection with the wild-type vector did not raise the HPRT mutation rate above background levels.

Figure 2B:
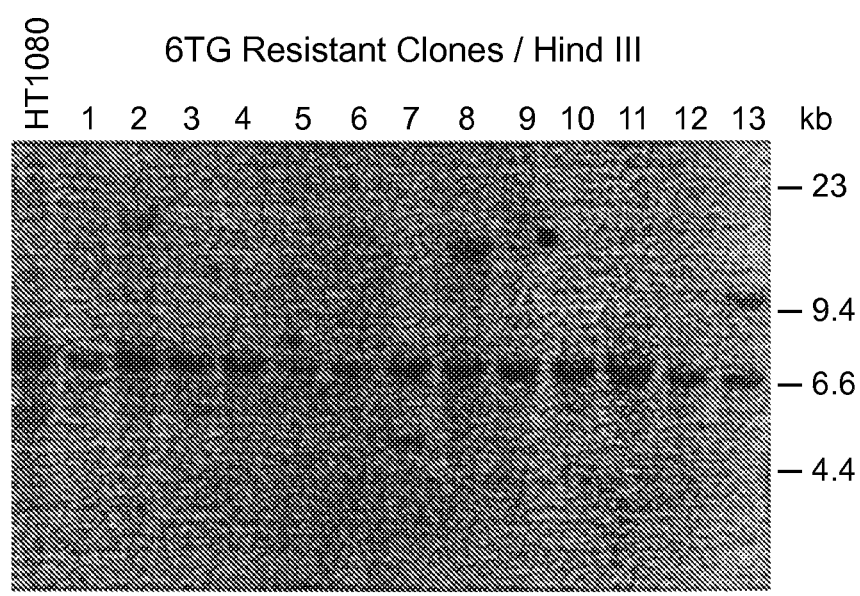
FIGS. 2B and 2C are autoradiograms of HT-1080 human fibrosarcoma cell genomic DNA that had been digested with HindIII (FIG. 2B) or HindIII plus PvuI (FIG. 2C). The lanes captioned "HT1080" shows hybridization of the probe shown in FIG. 2A to genomic DNA from unmodified HT1080 cells, and lanes 1-13 show hybridization of this probe to genomic DNA from thirteen different clones that were made 6TG resistant by transduction using the AAV vector AAV-HPe2/3X.
Figure 2C:
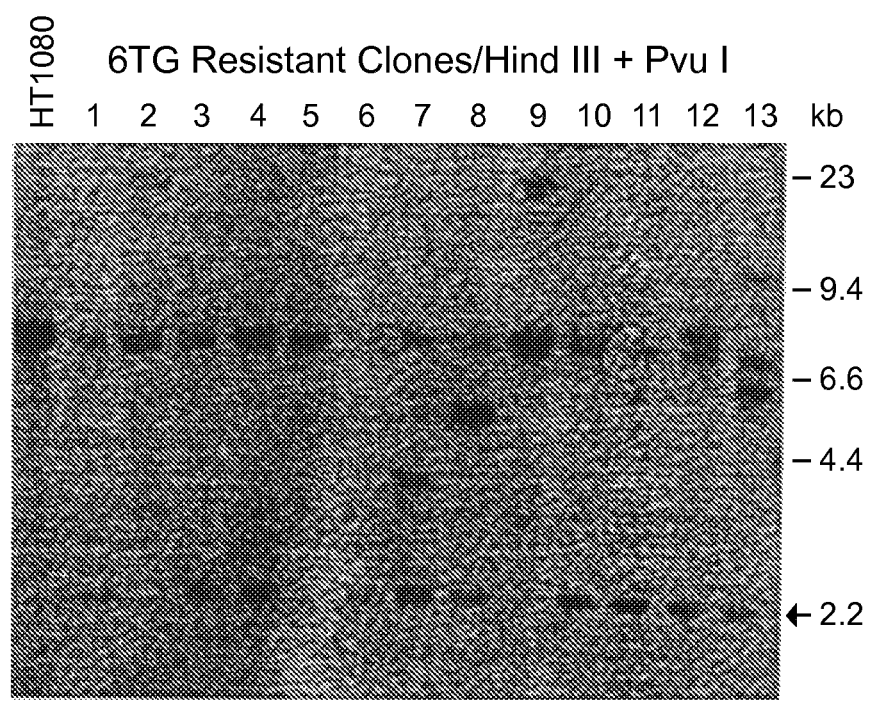

Southern analysis of several 6TG-resistant clones isolated after infection with AAV-HPe2/3X confirmed that the vector mutation had been introduced into the chromosomal HPRT locus. FIG. 2B shows the results of digestion with HindIII, which cuts outside of vector sequences and produces a 6.8 kb chromosomal fragment containing exons 2 and 3 in HT-1080 cells. This band was unaltered in all of the clones analyzed, demonstrating the absence of major rearrangements in this region. Five lines contained additional bands, presumably due to random vector integration. Further digestion with PvuI showed that 10/13 clones contained the 2.2 kb band expected from transfer of the vector PvuI site insertion mutation to the chromosome (FIG. 2C). To date we have analyzed 24 independent 6TG-resistant HT-1080 clones infected with AAV-HPe2/3X, 18 of which had the expected PvuI site insertion in exon 3 as determined by Southern analysis. We used the polymerase chain reaction (PCR) to amplify exon 3 from the genomic DNA of 6 of these clones and sequenced the PCR products (see Experimental Procedures). At least 330 by of unambiguous sequence was obtained from each clone, including all of exon 3. In all cases the entire sequence was identical to the published HPRT sequence except for the predicted 4 nucleotide insertion in exon 3. Clones without additional vector integration events were sequenced to avoid amplification of unlinked vector DNA. Sequence from the parental HT-1080 cell line did not contain this insertion mutation.

Example 3

The Effects of Vector Dose on Gene Correction

Figure 4:
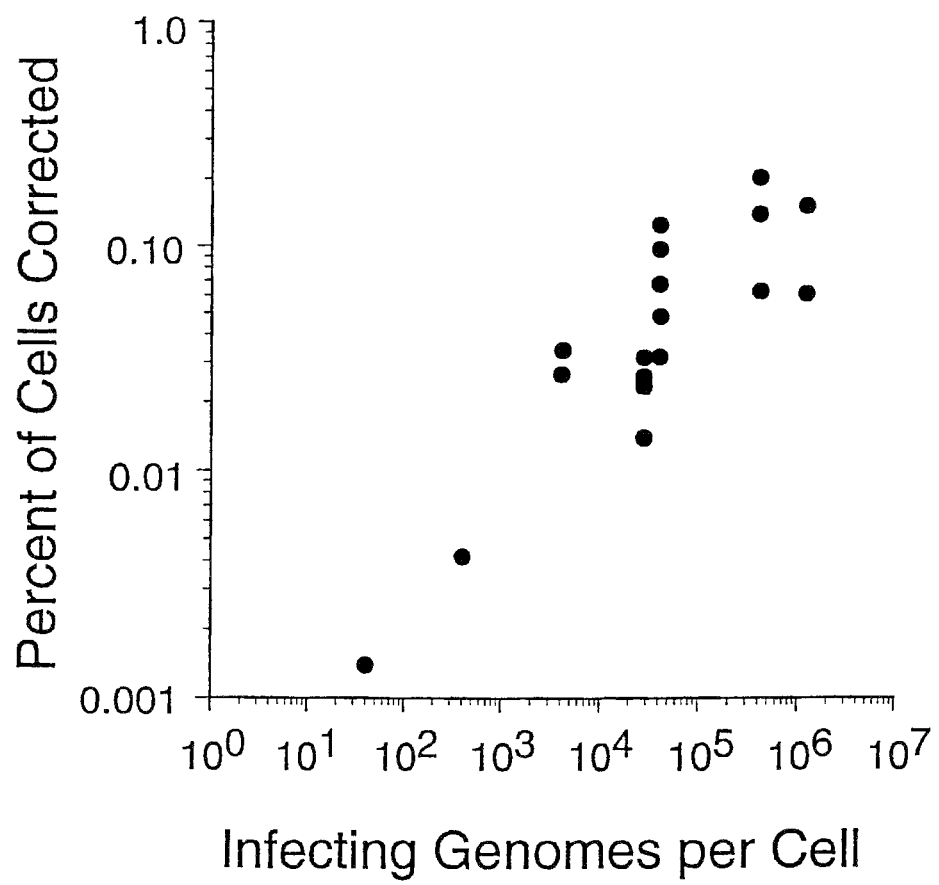
FIG. 4 presents the results of an analysis of the effect of multiplicity of infection on the frequency with which a defective neo gene present in HeLa cells is corrected by the AAV vector AAV-SNO648. This experiment is described in Example 3.

The mutant neo gene in HSNO39 cells was corrected with the AAV-SNO648 vector using a range of infection multiplicities. FIG. 4 shows the results of several experiments plotted as infecting vector genomes per cell versus the percent of cells with corrected neo genes. The gene correction rate increased from about 0.001 to greater than 0.1 percent with increasing vector doses of 40 to $2 \times 10^6$ vector particles per cell. These results suggest that the gene correction reaction is limited by the number of vector molecules entering the cell.

Example 4

Comparison of Transduction and Transfection Gene Correction Rates

Figure 5:
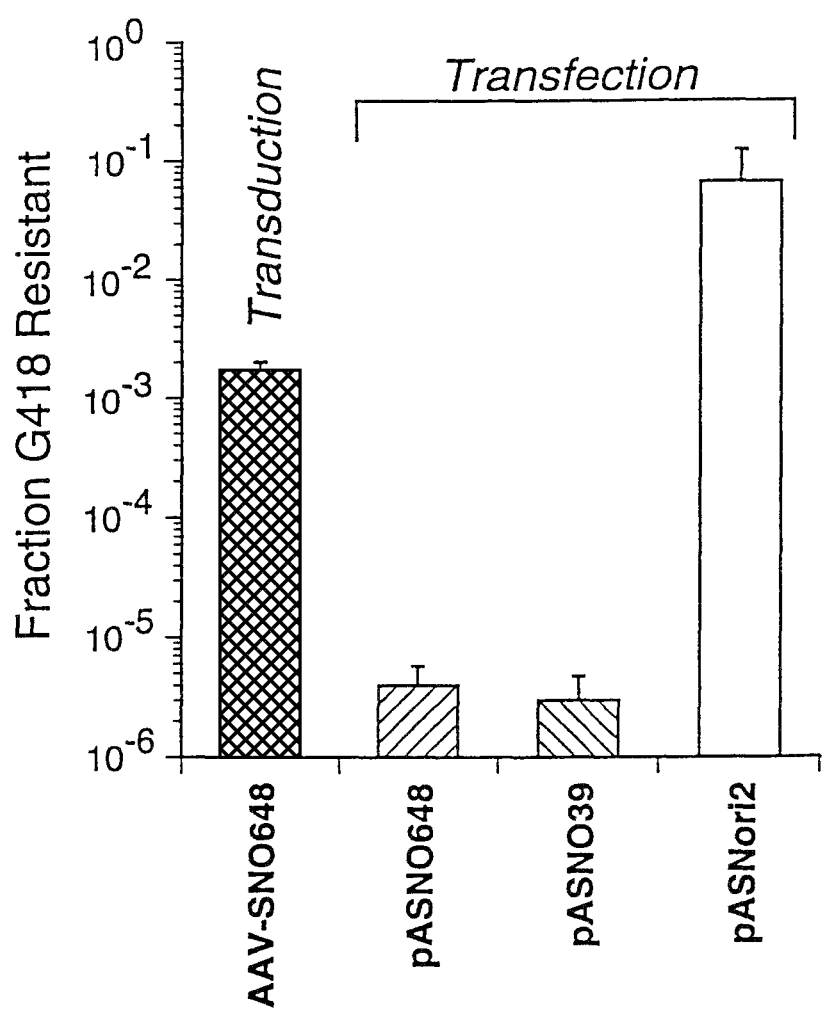
FIG. 5 shows a comparison of the frequency of neo gene correction in HSNO39 cells obtained using transduction versus transfection as described in Example 4. Transduction was carried out using the AAV vector AAV-SNO648, while transfection was performed using the plasmid pASNO648 (which contains the entire AAV-SNO648 genome), pASNO39 (which contains a mutation at base pair 39 of the neo gene) and pASNori2 (which has no neo mutation).

We compared neo gene correction rates in HSNO39 cells transduced with 25 AAV-SNO648 vector stocks or transfected with the plasmid pASNO648, which contains the entire AAV-SNO648 genome (FIG. 5). The transduction rate was at least 400 times that obtained by transfection. Further transfection experiments using the pASNO39 plasmid, which contains the same mutation as the HSNO39 cell line, gave similar results to pASNO648, suggesting that the gene correction rate of pASNO648 was actually due to reversion rather than homologous pairing. Thus the homologous pairing rate by transduction could have been much more than 400 times that obtained by transfection. One potential explanation for these differences is that plasmid uptake occurs in only a small proportion of transfected cells, while vector genomes presumably enter every cell. The stable transfection efficiency of HSNO39 cells was approximately 7% as determined by transfections with pASNori2, which is identical to pASNO648 except it contains a functional neo gene. Presumably, an even higher percentage of cells were transiently transfected. Even after making the conservative assumptions that 7% of transfected cells contained functional plasmid molecules, and that all the G418-resistant colonies obtained by transfecting pASNO648 were due to homologous pairing, the gene correction rate is still 30 fold higher in transduced cells than that observed in the subpopulation of cells that incorporated plasmid DNA ($1.7 \times 10^{-3}$ vs $5.7 \times 10^{-5}$).

Example 5

Modification of HPRT Genes in Normal Human Fibroblasts

Standard transduction experiments were performed by plating $5 \times 10^4$ normal human fibroblasts per well into 24 well plates. On day two, the medium was changed and vector stock (AAV-HPe2/3 or AAV-Hpe2/3X, prepared in DMEM) was added to the well. On day three, each well was treated with trypsin and the cells were plated into 10 cm dishes. On day four, all of the cells from each well were cultured without selection for 12-14 days to allow for elimination of existing HPRT protein in HPRT cells. The medium was changed every 3-4 days and when cells became too dense the cells were treated with trypsin and dilutions were plated into new dishes. After this phenotypic expression period, $10^5$, $10^4$, and $10^2$ cells of each culture were plated into new 10 cm dishes, and the following day 6TG (10 Tg/ml) was added to the $10^5$ and $10^4$ cell dishes. 6TG selection was not applied to the 102 cell dishes, as these were used to calculate plating efficiencies. The cells were cultured for ten additional days, stained with Coomassie brilliant blue G, and the surviving colonies were counted. The percentage of 6TG-resistant colony-forming units was determined after correcting for plating efficiencies. Four different normal fibroblast lines were studied: MHF1, MHF2 and MHF3 were from normal males, and FHF1 was from a normal female.

Figure 6:
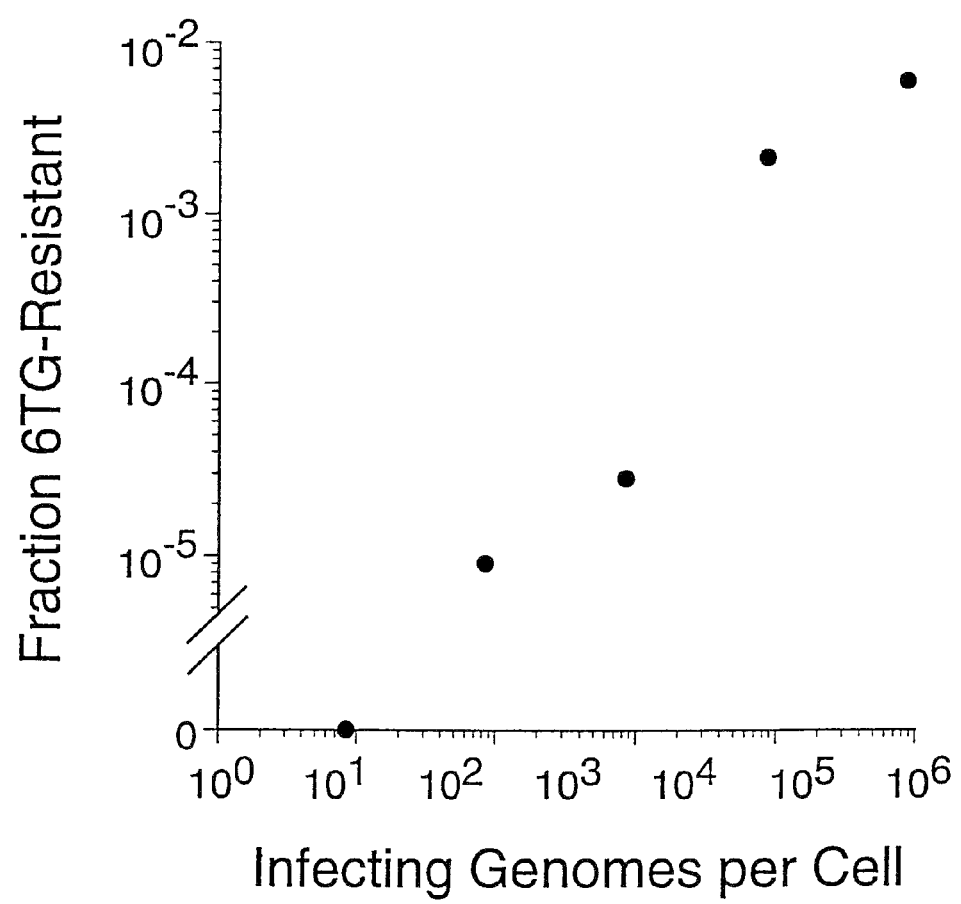
FIG. 6 shows the fraction of normal human fibroblasts having a modified HPRT gene after transduction using the AAV vector AAV-HPe2/3X as described in Example 5. The fraction of HPRT-modified cells is plotted versus the number of infecting AAV genomes per cell.
Figure 7:
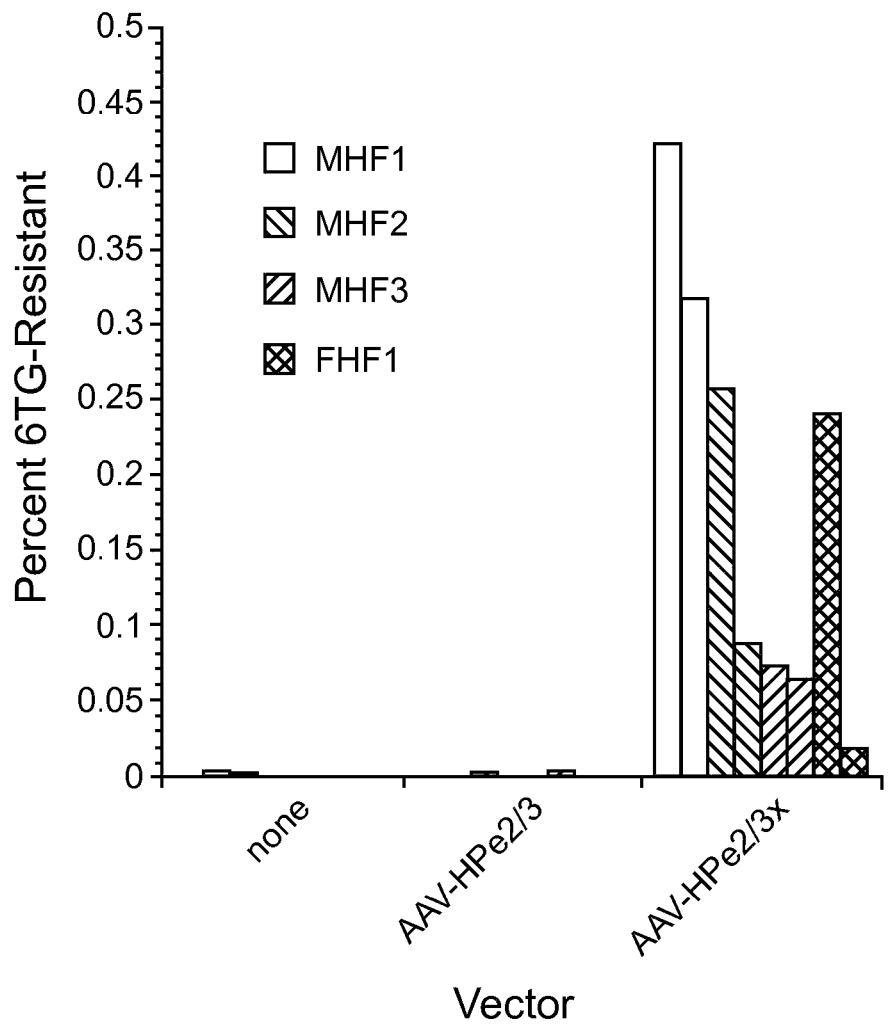
FIG. 7 presents the results of experiments in which four different normal human fibroblast cultures were transduced with either AAV-HPe2/3 (wild-type HPRT gene) or AAV-HPe2/3X (which introduces a frameshift mutation in the HPRT gene). The percent of HPRT gene modification is shown.

As shown in FIG. 6, modification of the HPRT gene was proportional to the number of infecting viral genomes per cell. Modifications could be introduced into the HPRT genes of all four fibroblast lines (FIG. 7).

Summary of Examples 1-5

These Examples demonstrates that vectors based on adeno-associated virus (AAV) efficiently and specifically modify vertebrate chromosomal target sequences. Both integrated neomycin phosphotransferase genes and the normal, X-linked hypoxanthine phosphoribosyltransferase gene were targeted by AAV vectors. Site-specific genetic modifications could be introduced into >0.1% of the total cell population, a significantly higher rate than could be achieved by transfection, and the modifications could be introduced into normal primary cells. The majority of modified cells contained no other detectable genetic changes, and DNA sequencing demonstrated the high fidelity of the process. These results suggest that parvoviral vectors are useful for introducing specific genetic changes into the genomic DNA of a wide variety of vertebrate cells.

Example 6

Assay System for Determining Efficiency of Gene Targeting

Figure 8:
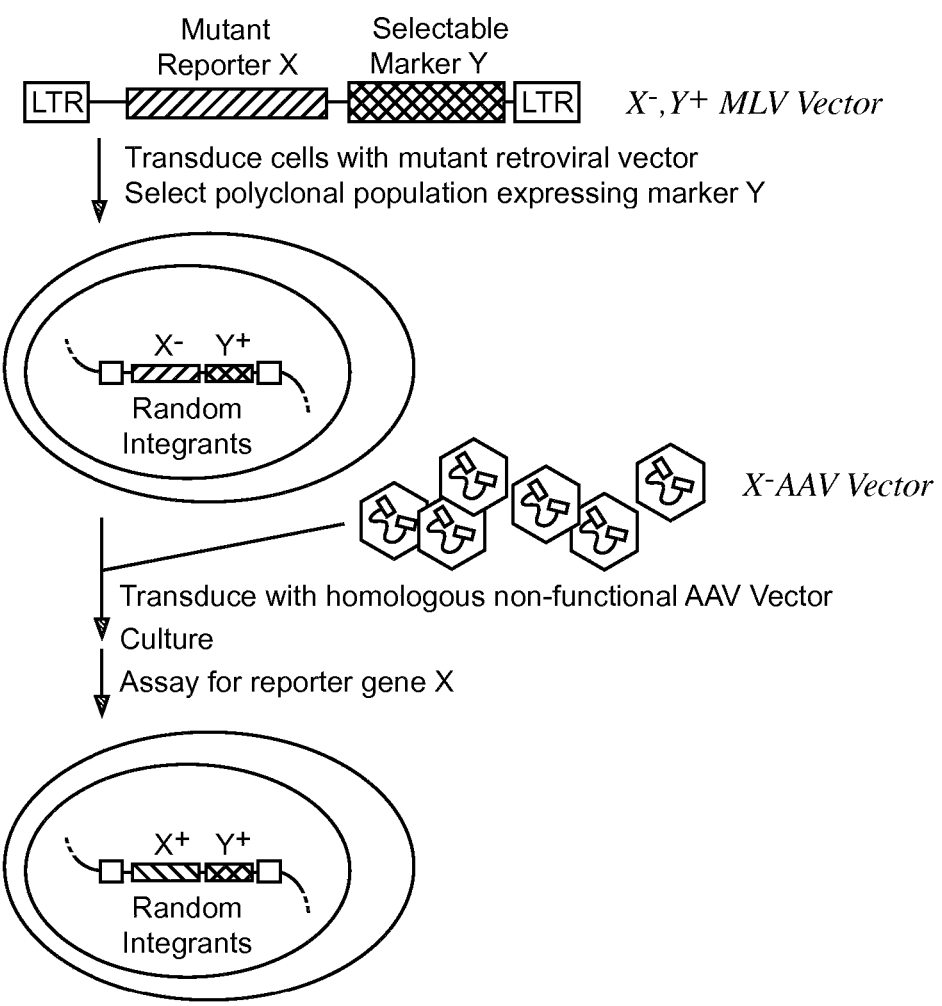
FIG. 8 shows a schematic representation of gene targeting at a retroviral vector target locus.

This Example describes a system for determining the efficiency of gene targeting. The system makes use of a bicistronic retroviral vector to introduce a target locus into the cells. The strategy employed is illustrated in FIG. 8.

A. Correction of Alkaline Phosphatase Genes

A human placental alkaline phosphatase (AP) reporter gene was used in this experiment. The LAPSN retroviral vector contains the AP gene under the control of the murine leukemia virus (MLV) LTR, and a neomycin resistance gene (neo) under the control of an internal SV40 early promoter (Miller et al. (1994) *Proc. Nat'l. Acad. Sci. USA* 91: 78-82). This vector was engineered to contain either a 4 by deletion at nucleotide 375 of the AP reading frame to create the vector LAP375(Δ4)SN, or a 2 by deletion at nucleotide 961 to create LA961(Δ2)SN (FIG. 8). Retroviral vector stocks were prepared by transient transfection of PG13 cells, with pseudotype vector particles in the gibbon ape leukemia virus (GALV) envelope (Miller et al. (1991) *J. Virol.* 65: 2220-2224). This pseudotype allows for efficient infection of human cells. Normal, primary human fibroblasts were transduced with LAP375(Δ4)SN/PG13 and selected in G418. A polyclonal population derived from more than 5,000 independent transduced cells was obtained, each of which presumably contained a different, single copy integration site of the retroviral target locus.

Figure 9:
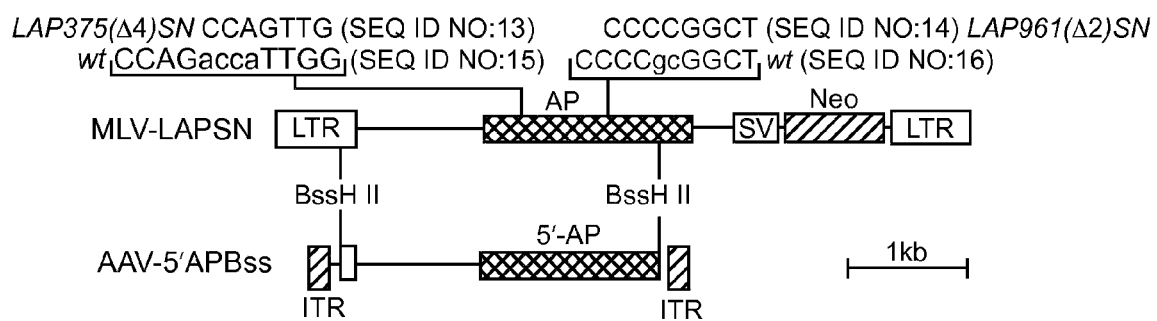
FIG. 9 shows vectors used for studies of gene targeting by repair of an alkaline phosphatase gene. Two retroviral vectors (MLV-LAPSN) are shown. The vector LAP375Δ4 has a 4 by deletion at nucleotide 375 of the AP reading frame, while the vector LAP961Δ2 has a two base pair deletion at nucleotide 961. Either of these vectors are introduced into host cells as a target locus for gene targeting. The AAV vector used for gene targeting (AAV-5'APBss) includes a portion of the AP gene.

An AAV vector, AAV-5'APBss, was prepared that contained the 5' portion of the AP gene (a 2486 by BssH II restriction fragment from pLAPSN; see FIG. 9). The fibroblast population containing LAP375(Δ4)SN was infected with the AAV-5'APBss vector at an MOI of 1,200 vector particles per cell, and the cells were cultured and stained for AP expression at different times after infection.

Figure 10:
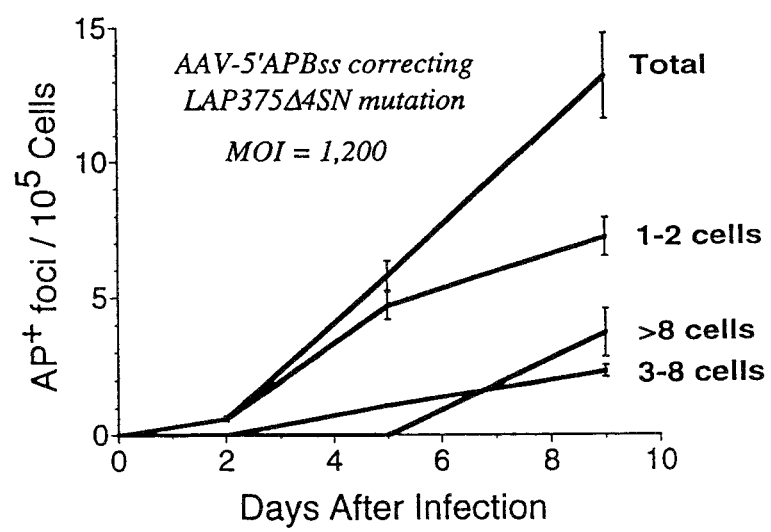
FIG. 10 shows a time course of gene targeting using the AP vector system.

As seen in FIG. 10, the number of AP$^+$ cell foci increased during the culture period, and the larger AP$^+$ foci only appeared at later times as expected. The number of small foci consisting of 1-2 AP$^+$ (presumably reflecting recent gene targeting events) also increased with time, suggesting that gene correction continued to occur over the entire culture period. This is not surprising, as AAV vector genomes persist for several days as episomal molecules in human fibroblasts (Russell et al. (1994) *Proc. Nat'l. Acad. Sci. USA* 91: 8915-8919). AP$^+$ cells were not observed among cells that did not contain the retroviral target, nor among those cells that did not receive the AAV vector. These controls rule out reversion mutation as a source of AP positivity. The absolute numbers of gene targeting events were similar to those obtained in HPRT targeting experiments using normal human fibroblasts at equivalent MOIs (Russell and Hirata (1998) *Nat. Genet.* 18: 325-330), which were relatively low in this experiment. Thus, these results demonstrate that the retroviral target system can be used in normal human cells as a convenient assay for measuring gene correction rates by AAV vectors.

B. Correction and Rescue of Neo Genes

In this experiment, gene correction at mutant neo genes in normal human cells was examined. The retroviral vector MLV-LHSNO39 was used to introduce mutant neo genes into normal human fibroblasts. MLV-LHSNO39 contains a functional hygromycin resistance gene and a neo gene with an insertion mutation at by 39 of the coding sequence. The vector also contains a p15A bacterial plasmid replication origin and a prokaryotic promoter controlling the neo gene, which allowed us to recover corrected proviruses as bacterial plasmids that confer resistance to kanamycin or neomycin.

Figure 11:
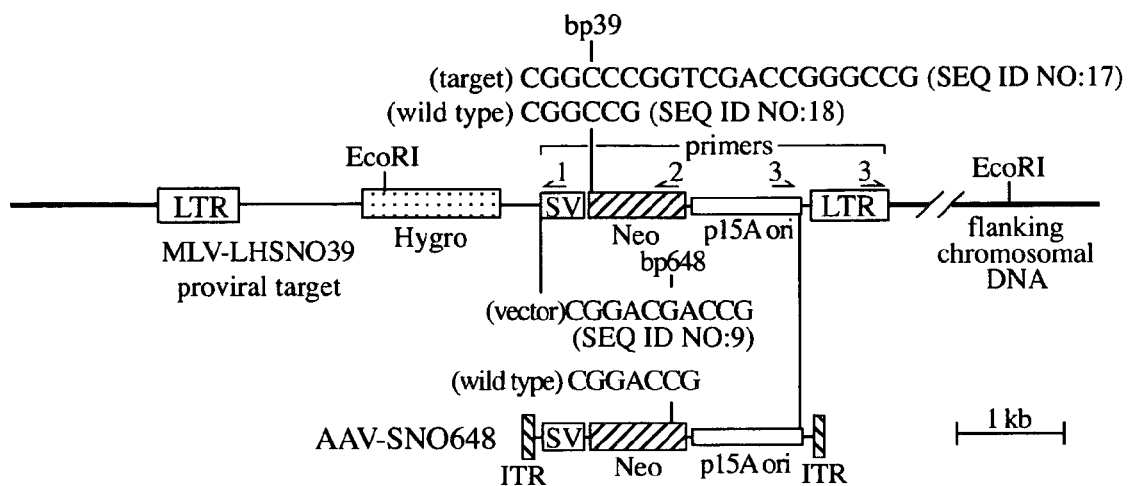
FIG. 11 shows a retroviral vector and an AAV vector that are suitable for use in testing the ability to correct a neo gene by gene targeting. The retroviral vector MLV-LHSNO39, which is introduced into the host cells as a target locus, has a neomycin resistance gene that contains an insertion mutation at by 39 of the neo gene. The AAV vector AAV-SNO648, includes a neo gene that has an insertion mutation at by 648 of the neo gene.

Normal human fibroblasts were transduced with MLV-LHSNO39, and hygromycin-resistant cells were selected. These cells were then transduced with the AAV vector AAV-SNO648, which has about 2.7 kb of sequence identity with the MLV¬ LHSNO39 vector, except that the neo gene is mutated at by 648 of the coding sequence and there is no mutation at by 39 (FIG. 11). Both neo mutations disrupt neo-function, so G418-resistant cells must have undergone a gene targeting event.

After infection with the AAV-SNO648 vector, approximately 1 in 1000 normal human fibroblasts containing the LHSNO39 target provirus became G418 resistant. This gene correction rate is similar to what was observed in HeLa cells containing the same neo mutation in Example 1 above.

Several G418-resistant colonies were isolated and expanded to approximately $10^6$-$10^7$ cells for DNA analysis (Table 3). Genomic DNA from each clone was digested with EcoRI, which digests the LHSNO39 targets once in the hygromycin resistance gene outside the region of homology with the AAV-SNO648 vector (FIG. 11). Genomic DNA fragments containing the corrected neo extend downstream to the next EcoRI site, which lies in the flanking chromosomal DNA, so they include the entire region homologous to the AAV-SNO648 vector, as well as regions just outside the region of homology to AAV-SNO648, and the junction between the retroviral provirus and chromosomal DNA. These fragments were circularized with DNA ligase and recovered in bacteria as plasmids conferring kanamycin or neomycin resistance. Table 3 summarizes the restriction digestion and sequence analysis to date of these recovered plasmids.

TABLE 3

Analysis of Corrected neo Genes Recovered as Bacterial Plasmids

| G418-Resistant Fibroblast Clone | Kan-Resistant Plasmids Recovered/ μg Genomic DNA | Size (kb) of Flanking Genomic DNA | Restriction Analysis | | Sequence Analysis | |
|---|---|---|---|---|---|---|
| | | | Left Homology End | Right Homology End | Left Homology End | Right Homology End |
| 1 | 210 | 1.0 | Rearranged | Intact | +14 by | ND |
| 2 | <2 | NA | NA | NA | NA | NA |

TABLE 3-continued

Analysis of Corrected neo Genes Recovered as Bacterial Plasmids

| G418-Resistant Fibroblast Clone | Kan-Resistant Plasmids Recovered/ μg Genomic DNA | Size (kb) of Flanking Genomic DNA | Restriction Analysis | | Sequence Analysis | |
|---|---|---|---|---|---|---|
| | | | Left Homology End | Right Homology End | Left Homology End | Right Homology End |
| 3  | 203 | 0.8 | Intact | Intact | Intact | ND |
| 4  | 497 | 0.5 | Intact | Intact | Intact | ND |
| 5  | 117 | 0.5 | Intact | Intact | Intact | ND |
| 6  | 167 | 0.3 | Intact | Intact | Intact | ND |
| 7  | 23  | 9.0 | Intact | Intact | Intact | ND |
| 8  | 110 | 3.0 | Intact | Intact | Intact | ND |
| 9  | <2  | NA  | NA     | NA     | NA     | NA |
| 10 | 200 | 6.5 | Intact | Intact | Intact | ND |
| 11 | 7   | 0.8 | Intact | Intact | Intact | ND |
| 12 | 120 | 1.2 | Intact | Intact | Intact | ND |

ND = not determined;
NA = not applicable

Of twelve independent G418-resistant fibroblast clones, ten contained corrected neo targets that could easily be recovered as bacterial plasmids. There was some variability in the efficiency of plasmid rescue, which presumably was related to differences in flanking chromosomal DNA sequences. In each case, a different plasmid was recovered, confirming that the retroviral proviruses were integrated at different chromosomal locations as expected. These rescued plasmids were digested with a panel of enzymes designed to determine if any major rearrangements occurred during the targeting process, especially at the left and right homology ends where the sequence of the AAV targeting vector diverges from that of the retroviral target. Based on restriction analysis, one of ten recovered targets had a rearrangement at the left homology end, and all ten of the right homology ends appeared intact. Sequencing confirmed that nine of ten rescued plasmids had no modifications at the left homology ends. Sequencing of the plasmid from clone #1 demonstrated that a rearrangement had occurred, which was in part due to an insertion of 14 additional non-homologous nucleotides from the AAV vector.

These rescue experiments and the sequence analysis of HPRT gene targeting (Example 2) demonstrate that AAV-mediated gene correction is usually a high fidelity process consisting of an accurate replacement of sequences at the intended modification site. In addition, the process does not usually introduce secondary mutations or rearrangements, even at the ends of homology. In the case of conventional gene targeting experiments based on electroporation, some studies (but not others (Thomas et al. (1992) *Mol. Cell. Biol.* 12: 2919-2923; Zheng et al. (1991) *Proc. Nat'l. Acad. Sci. USA* 88: 8067-8071) have suggested that secondary mutations can occur at the targeted locus (Brinster et al. (1989) *Proc. Nat'l. Acad. Sci. USA* 86: 7087-7091; Thomas and Capecchi (1986) *Nature* 324: 34-38), especially rearrangements at the homology ends (Doetschman et al. (1988) *Proc. Nat'l. Acad. Sci. USA* 85: 8583-8587; Hasty et al. (1991) *Mol. Cell. Biol.* 11: 4509-4517), so it was important to determine the fidelity of the AAV-mediated reaction. It should also be noted that we have never observed duplications at AAV-targeted loci, which are often produced by conventional gene targeting methods using insertion vectors.

These neo rescue experiments demonstrate several important points. Because the fibroblast population being studied contains many independent target loci at random chromosomal positions, we can conclude that AAV-mediated gene correction is not limited to particular loci (excluding any potential site preferences for retroviral integration). The fact that the process is a high fidelity gene correction event is crucial for use of this method for therapeutic purposes. In addition, this demonstration with neo targets allows one to more confidently interpret data with other retroviral targets such as the AP gene (above), where sequence analysis is more difficult. These studies also demonstrate the experimental potential of the retroviral target correction system, especially that targeted loci can be routinely recovered and analyzed as bacterial plasmids from normal human cells. Therefore, these experiments are readily adaptable to a wide variety of cell types and culture conditions which may require sequence analysis of targeted loci, not only to demonstrate fidelity but also to determine which mutations were introduced during gene correction.

C. Gene Correction in Other Cell Lines

A key feature of the retroviral target gene correction system described herein is its ability to be used in different cell types. This allows one to compare gene targeting rates at the same locus with the same vector in cell lines with various mutations in genes that may be important for gene targeting. As both the retroviral vectors used to introduce the targets and the AAV targeting vectors have broad host ranges, a large number of mutant cell lines can be studied. A particularly relevant set of cells are the primary human fibroblasts with mutations in genes involved in DNA repair and/or recombination, as these same genes could play a role in gene targeting. Many of these cell types are available from the Coriell Institute for Medical Research (Camden N.J.).

In this Example, four different primary human fibroblast cultures were used. These fibroblasts were isolated from normal males (MHF2), or patients with xeroderma pigmentosum (XP) complementation groups A (XPA1) or C(XPC1) and Bloom's Syndrome (BSI). Both diseases are associated with defects in DNA repair, with XP patients exhibiting increased sensitivity to ultraviolet light and Bloom's Syndrome patients having hypermutability.

Figure 12:
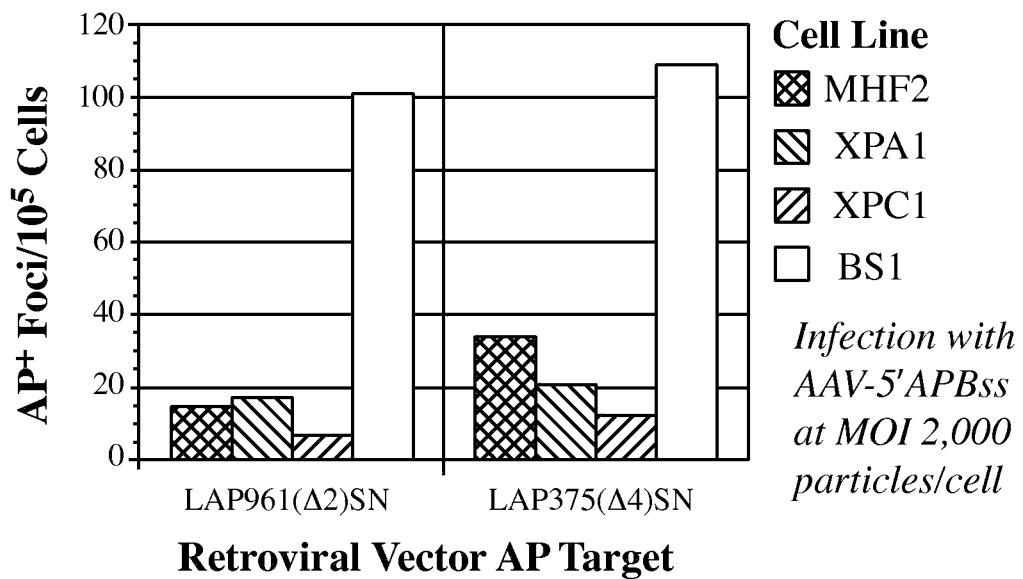
FIG. 12 shows the results of an experiment in which a mutant AP gene is corrected by gene targeting in normal (MHF2) and mutant fibroblasts (xeroderma pigmentosum complementation groups A (XPA1) and C(XPCI), and Bloom's Syndrome (BS1).

In order to measure gene correction rates we used the alkaline phosphatase (AP) gene targeting system shown in FIG. 9. All four fibroblast types were first transduced with the retroviral vectors LAP375(44)SN or LAP961(42)SN containing mutant AP genes and polyclonal G418-resistant populations were selected that consisted of more than 5,000 independent proviral integration events. These transduced fibroblasts were then infected with the AAV-5'APBss targeting vector, cultured for 8 days, and stained for AP expression. The gene correction rate was calculated as the number of $AP^+$ foci per $10^5$ infected cells. No $AP^+$ foci were observed in cultures that did not receive vector, nor in cultures that did not contain the retroviral vector target sites, confirming that AP expression was due to AAV-mediated gene correction. As shown in FIG. 12, there was little difference in gene targeting rates between the XP fibroblasts XPA1 and XPC1 as compared to the normal human fibroblasts MHF2. However, the Bloom's Syndrome fibroblasts BS1 has an approximately 5-fold higher gene correction rate with both retroviral targets. Since cells from Bloom's Syndrome patients are known to have increased rates of sister chromatid exchange (Chaganti et al. (1974) *Proc. Nat'l. Acad. Sci. USA* 71: 4508-4512), this suggests that gene targeting and sister chromatid exchange may involve similar mechanisms.

These experiments demonstrate that the retroviral target correction assay can be used on different cell lines, including primary fibroblast cultures. We have also used the system on HT-1080 human fibrosarcoma cells and HeLa cells, indicating that the methods are applicable to a wide range of cell types.

Example 7

In Vivo Correction of Chromosomal Genes

This Example describes methods for performing gene correction in vivo using the gene targeting methods of the invention. Two murine models are used, one with a mutation in the endogenous 11-glucuronidase gene (11-gus) and the other with engineered mutations in 13-galactosidase (f-gal) transgenes.

A. β-Gus Gene Correction In Vivo

A murine model of mucopolysaccharidosis type VII (MPS VII) is caused by a single base pair deletion in the β-gus gene (Sands and Birkenmeier (1993) *Proc. Nat'l. Acad. Sci. USA* 90: 6567-6571). Mice homozygous for the MPS VII mutation $gus^{mps}$ develop a lysosomal storage disease with characteristics similar to human MPS VII or Sly syndrome, including a shortened life span, skeletal abnormalities, and an accumulation of glycosaminoglycans in various tissues. These mice are an ideal model to study in vivo gene targeting for the following reasons. First, both the wild type and mutant genomic loci have been cloned and sequenced (Gallagher et al. (1987) *Genomics* 1: 145-152; Sands and Burkenmeier, supra.). Second, by using a histochemical stain (similar to staining for β-gal), $gus^+$ cells can easily be distinguished from $gus^{mps}$ cells in both tissue culture and tissue sections from several organs. Third, a biochemical assay for β-glucuronidase is available (Gallagher (1992). A PCR assay has been developed that distinguishes between mutant and wild type alleles (Wolfe and Sands (1996) Murine mucopolysaccharidosis type VII: a model system for somatic gene therapy of the central nervous system. In *Protocols for gene transfer in neuroscience: towards gene therapy of neurological disorders*, P. R. Lowenstein and L. W. Enquist, eds.; John Wiley and Sons, Ltd.). Transformed fibroblast cell lines from $gus^{mps}$ heterozygotes and homozygotes can be used for in vitro studies. Moreover, the mutation is a small (1 bp) deletion that is readily amenable to correction by AAV vectors.

Figure 13:
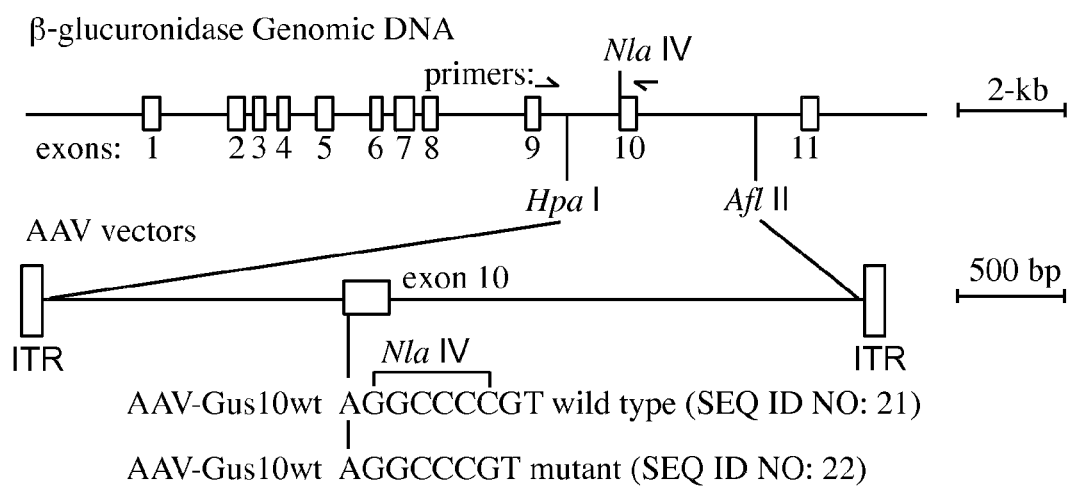
FIG. 13 shows the structure of the mouse β-glucuronidase genomic locus, and AAV vectors that are used in experiments to correct a mutation in the genomic β-glucuronidase locus.

The structure of the mouse β-gus genomic locus and AAV vectors that are suitable for use in the experiments are shown in FIG. 13. The AAV vectors contain approximately 4 kb of genomic DNA, including exon 10. The AAV-Gus10w5 vector is made from wild-type DNA, while the control vector AAV-Gus10mps contains the 1 by deletion in exon 10 that is responsible for MPS VII.

In initial experiments, the $gus^{mps}$ mutation is corrected in transformed fibroblasts from MPS VII mice in vitro, by infecting with the AAV-Gus10wt vector and then staining for β-gus expression. Cells infected with the AAV-Gus10mps vector will serve as a control. If gene correction occurs, β-gus expression is observed only in cells infected with the wild-type vector. As cultured mouse cells are generally more difficult to transduce with AAV vectors than mouse cells in vivo, this experiment is expected to provide a reasonable expectation that the vectors will also function in the in vivo experiments.

In vivo experiments are then performed on homozygous $gus^{mps}$ mice obtained by breeding heterozygotes and identified by PCR for $gus^{mps}$ alleles (Wolfe and Sands, supra.). The liver is used as a target tissue because β-gus is expressed at high levels in this organ. Moreover, AAV vectors are readily delivered to the liver (Koeberl et al. (1997) *Proc. Nat'l. Acad. Sci. USA* 94: 1426-1431; Snyder et al. (1997) *Nat. Genet.* 16: 270-276). Eight to 10 week old mice receive $10^{10}$ to $10^{11}$ vector particles, either by intravenous or intrahepatic injection. Previous gene addition studies indicate that both types of injection will efficiently deliver vector particles to the liver (Koeberl et al., supra.).

Mice are analyzed for β-gus gene correction at different times after infection (approximately 2 weeks, 2 months, and/or at the time of death). Based on the time course of AP gene targeting with AAV vectors (FIG. 10) and previous gene addition experiments using AAV vectors to deliver genes to the mouse liver (Snyder et al., supra.), it may take several days or weeks to reach a maximum gene correction level. The later time points will assess the persistence of gene expression from corrected alleles.

The analysis of injected mice can consist of staining tissue sections for β-gus expression, measuring β-glucuronidase activity in tissue homogenates, and isolating DNA from tissue samples for Southern analysis and PCR. The tissues to be examined can include liver, spleen, kidney, lung and brain. Individual $gus^+$ cells should be clearly visible in stained sections, allowing one to derive a gene correction rate based on estimates of the total cell number in the section or visualized field. A close examination of stained sections may also allow one to identify which types of cells are expressing β-gus. This histochemical analysis is expected to be the most sensitive assay for gene correction, with the ability to detect gene correction rates far below 1%. Based on gene targeting rates in vitro, the in vivo gene targeting rates are expected to be 0.1-1.0%. A comparison of sections from mice injected with AAV-Gus10wt and the control vector AAV-Gus10mps will demonstrate that the observed β-gus expression is due to specific correction of the $gus^{mps}$ by deletion mutation. Measurements of β-glucuronidase levels in tissue homogenates will also be performed to help determine the gene correction rate.

If the gene correction rate approaches 10%, one can most likely identify corrected chromosomal genes directly in Southern blots, since the wild-type allele can be digested by N1aIV, but the mutant allele cannot. Where the gene correction rate is lower, Southern analysis of genomic DNA samples can be performed in order to identify randomly integrated vector proviruses that may be present in addition to targeted loci (using restriction enzymes and/or probes from the AAV terminal repeats).

PCR analysis can also be used to identify corrected alleles. For example, one can amplify exon 10 using primers at the positions shown in FIG. 13. These PCR products should only be produced from genomic β-gus loci and not from randomly integrated vectors. Digesting the products with N1aIV will then distinguish corrected from mutant alleles, and should be able to detect even a relatively small fraction of wild-type, corrected alleles.

Similar gene correction experiments are also performed on newborn animals by injecting vectors into the superficial temporal vein (Sands et al. (1993) *Lab. Invest.* 68: 676-686). This approach has proven very successful in gene addition experiments with AAV vectors and should allow for vector delivery at a time when more cell proliferation is occurring. In addition, any therapeutic effect that may be due to gene correction must take place before the permanent damage that takes place in older animals. One can follow the development of the animals compared to uncorrected $gus^{mps}$ littermates and establish by microscopy techniques that a reduction in distended lysosomes has occurred (Wolfe and Sands, supra.).

B. β-Gal Transgene Correction In Vivo

A transgenic mouse model is also developed for in vivo gene correction experiments. This model is based on a β-gal shuttle transgene that can be rescued from mammalian cells as a bacterial plasmid that allows lac-bacteria to grow in media containing lactose. Transgenic mice containing mutated versions of the β-gal shuttle transgene are infected with AAV targeting vectors that can correct the β-gal mutation, and cells with corrected transgenes are detected by histochemical staining of tissue sections, similar to the experiments described above for β-gus gene correction. The major advantage of the β-gal system is that the corrected genes can be rescued in bacteria, providing an independent estimate of correction rates and allowing sequence analysis of targeted genes. In addition, by selecting mice with desirable transgene expression profiles, it is possible to perform gene correction experiments in a variety of different organs. The approach is similar to other transgenic animal models that screen for mutagenesis at β-gal transgenes (Gossen et al. (1994) Mutat. Res. 307: 451-459), except that in this case one is assaying for gene correction.

Figure 14:
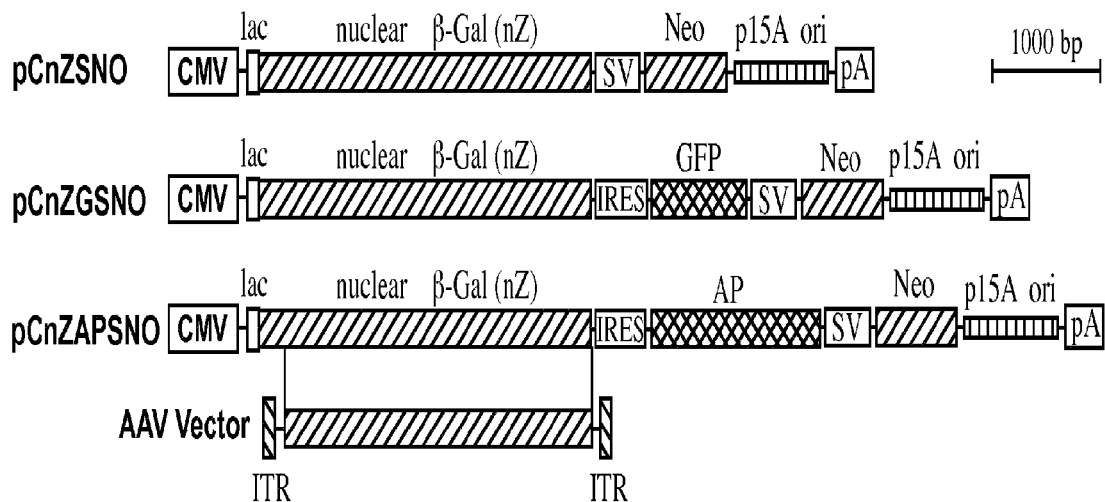
FIG. 14 shows 13-galactosidase transgenes that are introduced into transgenic animal cells (pCnZSNO, pCnZGSNO (green fluorescent protein reporter gene), and pCnZAPSNO (alkaline phosphatase reporter gene). An AAV vector that contains a portion of the β-gal coding sequence is also shown.

FIG. 14 shows constructs that can be used for these experiments (in linear form). pCnZSNO contains a nuclear-localizing β-gal gene under the control of the strong cytomegalovirus (CMV) promoter, a neo gene under the control of the SV40 early promoter, and a p15A plasmid origin. The SV-neo-p15A portion of the plasmid is the same shuttle vector cassette used in Example 6, which can replicate and confer kanamycin resistance in $E.\ coli$. The β-gene also contains a bacterial lac operator and promoter ("lac" in FIG. 14), which controls transcription in $E.\ coli$, allowing blue/white screening for corrected alleles and providing another prokaryotic selectable marker that confers lactose-dependent growth to lac bacteria. HeLa cells transfected with pCnZSNO form G418-resistant colonies with blue nuclei when stained for β-gal expression. Bacterial colonies can be selected for pCnZSNO by growing in media containing kanamycin or lactose as a sole sugar source.

Plasmid pCnZSNO can be further modified to contain additional marker genes that aid in identifying transfected cells expressing β-gal transgenes. Since mutations are to be introduced into β-gal for gene correction experiments, an additional marker for identification is necessary. For example, one can insert downstream reporter genes that are controlled by the same promoter as β-gal, but initiate translation from an internal ribosome entry site (IRES) derived from encephalomyocarditis virus. Plasmids with green fluorescent protein (GFP) and/or alkaline phosphatase (AP) can be constructed, for example, as shown in FIG. 14.

The pCnZGSNO and pCnZAPSNO plasmids are first tested in cultured cells. Mutations that disrupt protein function are engineered into the plasmid β-gal genes. HeLa cells are transfected with these mutated plasmids and stable integrants are selected in G418. Individual G418-resistant colonies are selected and tested for either GFP or AP expression by visualization under fluorescent light or histochemical staining. Colonies 20 expressing GFP or AP are then screened for gene correctability using an AAV vector that contains a wild type portion of β-gal (FIG. 14). The portion of β-gal included in the vector will not encode a functional β-gal protein. Corrected genes are identified both by staining HeLa cells for β-gal expression (which is analogous to the AP gene correction assay described previously), and by rescuing plasmids and screening bacterial colonies for β-gal expression.

The plasmid rescue experiments are similar to those described above, and consist of digesting integrated transgenes outside of the required genetic elements with restriction enzymes, circularizing the restriction fragments, electroporating bacteria, and then selecting either for kanamycin resistance (neo rescue) or growth in lactose-containing media (β-gal rescue). In the case of neo rescue experiments, one can also grow the colonies on Xp-gal plates and measure the percentage of recovered plasmids with corrected transgenes by blue/white colony screening. These in vitro experiments demonstrate that all the constructs required for gene correction are working properly.

Transgenic animals are then created by pronuclear injection of the appropriate pCnZGSNO or pCnZAPSNO constructs. Pups are screened for the presence of —the transgene by assaying for GFP expression under fluorescent light or AP expression by histochemical staining of tail or toe sections. Pups expressing the transgene are also analyzed by Southern blots to determine the structure of the transgene. These founders are bred and their offspring screened to determine which organs and tissues express the GFP or AP reporter genes. Presumably, the mutant β-gal transcripts will also be highly expressed in these same tissues, since it is controlled by the same promoter. The goal is to identify animals that express high levels of GFP or AP in a wide variety of tissues. Such animals will be versatile models to study in vivo gene correction.

Once the appropriate transgenic mice are identified, they are used for in vivo gene correction experiments. The AAV vectors to be used will contain either wild type β-gal sequences or a version of β-gal with the same mutation as present in the transgenic animal. Only the wild-type vector should result in gene correction. Eight to 10 week old mice are inoculated with $10^{10}$ to $10^{11}$ AAV vector particles by intravenous or intrahepatic injection, similarly to the experiments described above. These injections are expected to deliver vector mainly to the liver (Koeberl et al., supra.). Intramuscular injections are also performed in these transgenic animals, because AAV vectors have been found to efficiently transduce skeletal muscle in gene addition experiments (Fisher et al. (1997) Nat. Med. 3: 306-312; Xiao et al. (1996) J. Virol. 70: 8098-8108), and the procedure is simple to perform. In addition, intravenous injections can be performed on newborn animals as described above.

Animals are sacrificed at different times after injection (approximately 2 weeks, 2 months, and 12 months or at the time of death from other causes) and analyzed by several methods. First, tissue sections are stained histochemically for nuclear β-gal expression to determine the gene correction rate in the relevant organs. Second, DNA analysis is performed, including Southern blots and plasmid rescue in bacteria. Southern analysis is useful in determining the overall structure of the target locus and identifying random integration events that might also have occurred. Plasmid rescue is performed by selecting for either of the neo or β-gal genes, and the recovered plasmids are sequenced to demonstrate that gene correction occurred as predicted and to assess the fidelity of the reaction. The gene correction rate is also measured by blue/white staining of colonies for β-gal expression in plasmids recovered by neo gene selection.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A recombinant, replication-defective adeno-associated virus (AAV) viral particle for introducing a genetic modification of a preselected target gene in the genome of a vertebrate cell by homologous recombination, the recombinant, replication-defective AAV viral particle comprising:
   a targeting construct comprising a genomic DNA sequence which is substantially identical to the preselected target gene sequence except for the modification to be introduced;
   wherein the genomic DNA sequence consists of less than an entire copy of the preselected target gene;
   wherein the modification to be introduced is flanked by two regions of nucleotide sequence which are substantially identical to the preselected target gene sequence, each region being at least 100 nucleotides in length;
   wherein the targeting construct comprises two AAV inverted terminal repeats (ITRs), one at each end of the targeting construct;
   wherein the modification comprises one or more insertions or substitutions or a combination thereof; and
   wherein the viral particle introduces the modification into the preselected target gene by homologous recombination at a frequency of at least 0.01%.

2. The recombinant viral particle of claim 1, wherein the preselected target gene sequence comprises a DNA sequence selected from the group consisting of a transcriptional regulatory region, a splice signal, a sequence involved in DNA replication, a matrix attachment point, a chromosomal recombination hotspot, a structural gene, or a coding region for a signal sequence, and portions thereof.

3. The recombinant viral particle of claim 2, wherein the DNA sequence comprises a structural gene and the modification results in an amino acid substitution, insertion, or a combination thereof, in a polypeptide encoded by the gene.

4. The recombinant viral particle of claim 2, wherein the DNA sequence comprises a transcriptional regulatory region selected from the group consisting of a promoter, an enhancer, a response element, a transcription termination signal, and a locus control region.

5. The recombinant viral particle of claim 4, wherein a gene under the control of the modified transcriptional regulatory region is expressed at a different level than that at which the gene is expressed under equivalent conditions when the gene is under the control of the unmodified transcriptional regulatory region.

6. The recombinant viral particle of claim 1 wherein the targeting construct includes a recombination signal that is flanked by the nucleotide sequences that are substantially identical to the preselected target gene.

7. The recombinant viral particle of claim 6 wherein the recombination signal is one or more Lox sites.

8. The recombinant viral particle of claim 1 wherein the targeting construct further comprises a selectable marker.

9. The recombinant viral particle of claim 8 wherein the selectable marker comprises the neo gene or hyg gene.

10. The recombinant viral particle of claim 1 wherein the targeting construct further comprises a screenable marker.

11. The recombinant viral particle of claim 10 wherein the screenable marker comprises a gene encoding β-galactosidase, β-glucuronidase, luciferase, alkaline phosphatase or a fluorescent maker.

12. The recombinant viral particle of claim 1 wherein the targeting construct further comprises a targeting enhancer.

13. The recombinant viral particle of claim 1 wherein the AAV rep and cap genes have been deleted.

14. The recombinant viral particle of claim 1 comprising two targeting constructs.

15. The recombinant viral particle of claim 1, comprising a capsid having one or more modifications to improve cell targeting.

16. The recombinant viral particle of claim 1 wherein the viral particle consists essentially of particles comprising either all plus or all minus strands.

17. The recombinant viral particle of claim 1 wherein the targeting construct further comprises a DNA that is exogenous to the vertebrate cell, wherein the exogenous DNA is preselected for modification of the genomic target locus.

18. The recombinant viral particle of claim 17, wherein the exogenous DNA comprises a selection marker that is functional in the vertebrate cell.

19. The recombinant viral particle of claim 1, wherein the viral particle introduces the modification into the preselected target gene by homologous recombination at a frequency of at least 0.1%.

20. The recombinant viral particle of claim 1, wherein the viral particle introduces the modification into the preselected target gene by homologous recombination at a frequency of at least 1%.

\* \* \* \* \*

SEQUENCE LISTING

<160> NUMBER OF SEQ ID NOS: 22

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence: Sequencing
      primer for neomycin resistance gene.

<400> SEQUENCE: 1
atggctttct tgccgcca                                                 18

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Sequencing
      primer for neomycin resistance gene.

<400> SEQUENCE: 2
atacgcttga tccggctac                                                19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: PCR primer
      for neomycin resistance gene.

<400> SEQUENCE: 3
ccttatgaaa catgagggca aagg                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: PCR primer
      for neomycin resistance gene.

<400> SEQUENCE: 4
tgtgacacag gcagactgtg gatc                                          24

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: DNA
      sequencing primer for neomycin resistance gene.

<400> SEQUENCE: 5
acctactgtt gccacta                                                  17

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Sal I
      linker.

<400> SEQUENCE: 6
cggtcgaccg                                                          10

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Neomycin
      resistance gene sequence bp 35-40 with 14
      nucleotide insertion at 39.

<400> SEQUENCE: 7
cggcccggtc gaccgggccg                                                    20

<210> SEQ ID NO 8
<211> LENGTH: 6
<212> TYPE: DNA
<213> ORGANISM: Escherichia coli

<400> SEQUENCE: 8 cggccg                                                                    6

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Neomycin
      resistance gene sequence bp 644-650 with 3
      nucleotide insertion at 648.

<400> SEQUENCE: 9
cggacgaccg                                                               10

<210> SEQ ID NO 10
<211> LENGTH: 7
<212> TYPE: DNA
<213> ORGANISM: Escherichia coli

<400> SEQUENCE: 10 cggaccg                                                                   7

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Human HPRT
      gene, exon 3, with 4 nucleotide insertion.

<400> SEQUENCE: 11
ctcgatcgag                                                               10

<210> SEQ ID NO 12
<211> LENGTH: 6
<212> TYPE: DNA
<213> ORGANISM: Homo sapiens

<400> SEQUENCE: 12 ctcgag                                                                    6

<210> SEQ ID NO 13
<211> LENGTH: 8
<212> TYPE: DNA
<213> ORGANISM: Artificial Sequence
<220> FEATURE:
<223> OTHER INFORMATION: Description of Artificial Sequence: Human placental alkaline phosphatase gene with 4 base
    deletion.

<400> SEQUENCE: 13 ccagttgg                                                                    8

<210> SEQ ID NO 14
<211> LENGTH: 8
<212> TYPE: DNA
<213> ORGANISM: Artificial Sequence
<220> FEATURE:
<223> OTHER INFORMATION: Description of Artificial Sequence: Human
    placental alkaline phosphatase gene with 2 base
    deletion.

<400> SEQUENCE: 14 ccccggct                                                                    8

<210> SEQ ID NO 15
<211> LENGTH: 12
<212> TYPE: DNA
<213> ORGANISM: Homo sapiens

<400> SEQUENCE: 15
ccagaccatt gg                                                              12

<210> SEQ ID NO 16
<211> LENGTH: 10
<212> TYPE: DNA
<213> ORGANISM: Homo sapiens

<400> SEQUENCE: 16
ccccgcggct                                                                 10

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Neomycin
    resistance gene sequence bp 35-40 with 14
    nucleotide insertion at 39.

<400> SEQUENCE: 17
cggcccggtc gaccgggccg                                                      20

<210> SEQ ID NO 18
<211> LENGTH: 6
<212> TYPE: DNA
<213> ORGANISM: Escherichia coli

<400> SEQUENCE: 18 cggccg                                                                      6

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Neomycin
    resistance gene sequence bp 644-650 with 3
    nucleotide insertion at 648.

<400> SEQUENCE: 19
cggacgaccg                                                                 10

```
<210> SEQ ID NO 20
<211> LENGTH: 7
<212> TYPE: DNA
<213> ORGANISM: Escherichia coli

<400> SEQUENCE: 20 cggaccg                                                                   7

<210> SEQ ID NO 21
<211> LENGTH: 9
<212> TYPE: DNA
<213> ORGANISM: Mus musculus

<400> SEQUENCE: 21 aggccccgt                                                                 9

<210> SEQ ID NO 22
<211> LENGTH: 8
<212> TYPE: DNA
<213> ORGANISM: Artificial Sequence
<220> FEATURE:
<223> OTHER INFORMATION: Description of Artificial Sequence: Portion of
      murine beta-glucuronidase gene sequence with 1
      base deletion.

<400> SEQUENCE: 22 aggcccgt                                                                  8
```